(12) United States Patent
Rizzo et al.

(10) Patent No.: US 6,976,998 B2
(45) Date of Patent: Dec. 20, 2005

(54) MINIMALLY INVASIVE RETINAL PROSTHESIS

(75) Inventors: Joseph F. Rizzo, Boston, MA (US); John L. Wyatt, Jr., Sudbury, MA (US); Luke Theogarajan, Somerville, MA (US)

(73) Assignees: Massachusetts Institute of Technology, Cambridge, MA (US); Massachusetts Eye & Ear Infirmary, Boston, MA (US)

( * ) Notice: Subject to any disclaimer, the term of this patent is extended or adjusted under 35 U.S.C. 154(b) by 62 days.

(21) Appl. No.: 10/346,701

(22) Filed: Jan. 17, 2003

(65) Prior Publication Data

US 2003/0158588 A1 Aug. 21, 2003

Related U.S. Application Data

(60) Provisional application No. 60/349,687, filed on Jan. 17, 2002.

(51) Int. Cl.$^7$ ................................................ A61F 2/16
(52) U.S. Cl. ...................................... 623/6.63; 607/54
(58) Field of Search ...................... 607/53, 54; 623/60, 623/63, 6.63

(56) References Cited

U.S. PATENT DOCUMENTS

| | | | |
|---|---|---|---|
| 2,760,483 A | 8/1956 | Tassicker | |
| 4,551,149 A | 11/1985 | Sciarra | 623/4 |
| 4,628,933 A | 12/1986 | Michelson | 128/419 |
| 5,016,633 A | 5/1991 | Chow | 128/419 |
| 5,024,223 A | 6/1991 | Chow | 128/419 |
| 5,109,844 A | 5/1992 | de Juan, Jr. et al. | 128/419 |
| 5,147,284 A | 9/1992 | Fedorov et al. | 600/9 |
| 5,159,927 A | 11/1992 | Schmid | 128/419 |
| 5,397,350 A | 3/1995 | Chow et al. | 623/4 |
| 5,411,540 A | 5/1995 | Edell et al. | 607/53 |
| 5,554,187 A | 9/1996 | Rizzo, III | 623/6 |
| 5,556,423 A | 9/1996 | Chow et al. | 607/54 |
| 5,575,813 A | 11/1996 | Edell et al. | 607/16 |
| 5,597,381 A | 1/1997 | Rizzo, III | 623/4 |
| 5,674,263 A | 10/1997 | Yamamoto et al. | 607/54 |
| 5,800,530 A | 9/1998 | Rizzo, III | 623/6 |
| 5,836,996 A | 11/1998 | Doorish | 607/54 |
| 5,837,995 A | 11/1998 | Chow et al. | 250/214 |
| 5,865,839 A | 2/1999 | Doorish | 607/54 |
| 5,873,901 A | 2/1999 | Wu et al. | 607/54 |

(Continued)

FOREIGN PATENT DOCUMENTS

EP 0 460 320 11/1991

(Continued)

OTHER PUBLICATIONS

International Search Report for PCT/US 03/01386 mailed Jun. 27, 2003, and published with WO 03/061537 on Jul. 31, 2003.

*Primary Examiner*—Corrine McDermott
*Assistant Examiner*—Thomas J Sweet
(74) *Attorney, Agent, or Firm*—Choate, Hall & Stewart LLP

(57) ABSTRACT

An ocular device that can more safely and effectively perform all functions needed of a retinal prosthesis with electronic components that are placed outside the wall of an eye, are powered wirelessly provided by an external power source, and which provide a patient with a view determined by natural motion of the eye and triggered by natural incident light converging at the retina. In one aspect, the invention is an externally powered, light-activated, sub-retinal prosthesis in which natural light entering the eye conveys visual details to the sub-retinal prosthesis, while wireless radiofrequency transmission provides the power needed to stimulate the retina, which would be insufficient if it were obtained from the intensity of incoming light alone.

15 Claims, 7 Drawing Sheets

U.S. PATENT DOCUMENTS

| | | | |
|---|---|---|---|
| 5,895,415 A | 4/1999 | Chow et al. | 607/54 |
| 5,935,155 A | 8/1999 | Humayun et al. | 607/54 |
| 5,944,747 A | 8/1999 | Greenberg et al. | 607/54 |
| 5,949,064 A | 9/1999 | Chow et al. | 250/214 |
| 6,020,593 A | 2/2000 | Chow et al. | 250/551 |
| 6,069,365 A | 5/2000 | Chow et al. | 250/551 |
| 6,075,251 A | 6/2000 | Chow et al. | 250/551 |
| 6,120,538 A | 9/2000 | Rizzo, III et al. | 623/6.11 |
| 6,165,192 A | 12/2000 | Greenberg et al. | 606/185 |
| 6,201,234 B1 | 3/2001 | Chow et al. | 250/214 |
| 6,230,057 B1 | 5/2001 | Chow et al. | 607/54 |
| 6,298,270 B1 | 10/2001 | Nisch et al. | 607/54 |
| 6,324,429 B1 | 11/2001 | Shire et al. | 607/54 |
| 6,347,250 B1 | 2/2002 | Nisch et al. | 607/54 |
| 6,368,349 B1 | 4/2002 | Wyatt et al. | 623/6.63 |
| 6,389,317 B1 | 5/2002 | Chow et al. | 607/54 |
| 6,393,327 B1 | 5/2002 | Scribner | 607/54 |
| 6,400,989 B1 | 6/2002 | Eckmiller | 607/54 |
| 6,427,087 B1 | 7/2002 | Chow et al. | 607/54 |
| 6,442,431 B1 | 8/2002 | Veraart et al. | 607/54 |
| 6,458,157 B1 | 10/2002 | Suaning | 623/6.63 |
| 6,533,798 B2 | 3/2003 | Greenberg et al. | 606/185 |
| 6,611,716 B2 | 8/2003 | Chow et al. | 607/54 |
| 2002/0002362 A1 | 1/2002 | Humayun et al. | 604/521 |
| 2002/0002381 A1 | 1/2002 | Greenberg et al. | 606/185 |
| 2002/0010496 A1 | 1/2002 | Greenberg et al. | 607/54 |
| 2002/0038134 A1 | 3/2002 | Greenberg et al. | 607/1 |
| 2002/0042638 A1 | 4/2002 | Iezzi et al. | 607/88 |
| 2002/0091421 A1 | 7/2002 | Greenberg et al. | 607/54 |
| 2002/0091422 A1 | 7/2002 | Greenberg et al. | 607/54 |
| 2002/0095193 A1 | 7/2002 | Ok et al. | 607/54 |
| 2002/0111655 A1 | 8/2002 | Scribner | 607/54 |
| 2002/0111658 A1 | 8/2002 | Greenberg et al. | 607/116 |
| 2002/0120296 A1 | 8/2002 | Mech et al. | 607/2 |
| 2002/0139556 A1 | 10/2002 | Ok et al. | 174/50.6 |
| 2002/0161417 A1 | 10/2002 | Scribner | 607/54 |
| 2002/0177895 A1 | 11/2002 | Nisch | 623/5.11 |
| 2002/0193845 A1 | 12/2002 | Greenberg et al. | 607/54 |
| 2002/0198573 A1 | 12/2002 | Nisch et al. | 607/54 |
| 2003/0014089 A1 | 1/2003 | Chow et al. | 607/54 |
| 2003/0028225 A1 | 2/2003 | Chow et al. | 607/54 |
| 2003/0069603 A1 | 4/2003 | Little et al. | 606/219 |
| 2003/0097165 A1 | 5/2003 | Krulevitch et al. | 607/115 |
| 2003/0097166 A1 | 5/2003 | Krulevitch et al. | 607/116 |
| 2003/0130699 A1 | 7/2003 | Kelly et al. | 607/5 |
| 2003/0149458 A1 | 8/2003 | Williamson et al. | 607/54 |
| 2003/0181957 A1 | 9/2003 | Greenberg et al. | 607/54 |
| 2003/0187491 A1 | 10/2003 | Greenberg et al. | 607/116 |
| 2003/0195601 A1 | 10/2003 | Hung et al. | 607/116 |
| 2003/0216747 A1 | 11/2003 | Kaplan | 606/107 |

FOREIGN PATENT DOCUMENTS

| | | |
|---|---|---|
| WO | WO 98/13665 | 4/1998 |
| WO | WO 98/17343 | 4/1998 |
| WO | WO 98/17344 | 4/1998 |
| WO | WO 98/51206 | 11/1998 |
| WO | WO 99/15119 | 4/1999 |
| WO | WO 00/67676 | 11/2000 |
| WO | WO 00/67838 | 11/2000 |
| WO | WO 02/056758 | 7/2002 |
| WO | WO 02/064072 | 8/2002 |
| WO | WO 02/080816 | 10/2002 |
| WO | WO 02/080828 | 10/2002 |
| WO | WO 03/092564 | 11/2003 | ns # MINIMALLY INVASIVE RETINAL PROSTHESIS

CROSS-REFERENCE TO RELATED APPLICATIONS

The present application claims priority to U.S. Provisional Application No. 60/349,687, filed Jan. 17, 2002, the teachings of which are incorporated herein by reference.

STATEMENT OF GOVERNMENT SUPPORT

This invention was made with government support under Grant Nos. BES-0001296 and BES-0201861, awarded by NIH. The U.S. Government has certain fights in the invention.

FIELD OF THE INVENTION

The present invention is directed to the field of ocular devices and more particularly to an apparatus and method for a minimally invasive retinal prosthesis.

BACKGROUND OF THE INVENTION

A reference list is appended hereto. Citation numbers identified in parentheses refer to this reference list. All of the teachings of the references identified in the reference list are incorporated herein by reference.

A visual prosthesis is a device that captures aspects of the visual environment and uses this information to stimulate nerves within the visual pathway to influence vision. (40, 60, 61, 76, 77, 85, 114, 115, 116, 136, 142). A visual prosthesis may be placed within the eye or at some location on the path toward or within the visual part of the brain. Visual prosthetic devices within the eye can be positioned on the inner surface of the retina (i.e. epi-retinal) or under the retina (sub-retinal). Every option for placement provides certain advantages and creates certain disadvantages that must be addressed if vision is to be created in a manner that would be useful to a blind patient.

A retinal prosthesis is designed to replace the function of degenerated nerve cells of an eye that causes in blindness. The retinal prosthesis has the capability to stimulate surviving nerve cells in a manner designed to convey information about the visual world. The surviving nerve cells of the eye carry the artificially induced nerve signals to the visual part of the brain through the optic nerve. The broad concept of utilizing a retinal prosthesis to restore vision to the blind was first described in U.S. Pat. No. 2,760,483 to Tassicker and later in U.S. Pat. No. 4,628,933 to Michelson, the teachings of both of which are incorporated herein by reference.

At least two significant forms of blindness occur because of a loss of the photoreceptive cells of the retina, i.e. those cells that normally convert the energy from light that enters the eye into a nerve signal that is carried to the brain. Age-related macular degeneration is the leading cause of blindness in the industrialized world, and retinitis pigmentosa is the leading cause of inherited blindness throughout the world. Age-related macular degeneration results in a loss of central vision, which eliminates a person's ability to read or recognize faces. Retinitis pigmentosa results in a slow loss of peripheral and then central vision. Patients with retinitis pigmentosa are more severely affected because of the loss of both central and peripheral vision. A worthy goal of treatment for patients with retinitis pigmentosa is restoration of some peripheral vision, which would enhance a patient's ability to ambulate independently and more safely in unfamiliar environments. A retinal prosthesis has the potential to restore vision to patients with these and potentially other forms of blindness caused by a dysfunctional retina.

Retinal prostheses can be broadly divided into two categories: epi-retinal (30, 63, 64, 66, 81, 83, 105, 106, 109, 111, 136, 142) and sub-retinal. (14, 15, 26, 28, 29, 119, 120, 121, 129–132). Epi-retinal devices are placed on or near the inner surface of the retina, that is, the side which is first exposed to incoming light rays and along which the nerve fibers of the ganglion cells pass on their way to the optic nerve. Sub-retinal devices are placed under the retina, between the retina and the underlying retinal pigment epithelium or other deeper tissues. Although devices in either location are capable of effectively stimulating retinal nerve cells, there are advantages and potential disadvantages to each strategy. One very significant advantage of a sub-retinal prosthesis is the opportunity to implant the device by approaching the sub-retinal space from outside of the eye (i.e. ab externo, through the sclera covering the back of the eye), rather than having to perform any (or any significant) surgery within the center of the eye, which is much more likely to result in chronic inflammation, infection or a host of other problems that might compromise the safe implantation or effectiveness of a prosthesis.

Retinal prostheses can also be divided into the means by which they receive power for their operation. Any retinal prosthesis must embody the means to: 1) capture a visual image; 2) translate the details of a captured visual image into a pattern of stimulation of the retina; and 3) obtain sufficient power to both operate the electronics and stimulate the retina. Retinal prostheses have been disclosed which use electromagnetic energy obtained either from light (119–132) or radiofrequency (136–142) transmission.

A third division of retinal prostheses is by the location at which the image from the external world is acquired. An external camera located on a pair of glasses or elsewhere outside the body is one possibility, while an imaging system implanted within the eye is another. An external camera has the advantage of faithfully capturing details of a visual scene but this signal must be then be transformed to a pattern of stimulation commands sent to the implanted prosthesis. An additional disadvantage is that, in simple implementations, the view the patient sees is determined artificially by motion of the external camera rather than by the natural motion of the eye. An internal imaging system has the advantage of allowing the direction of the eye to determine what the patient sees, but the imaging system must be implanted within the body and the exact stimulation pattern applied to the retina is not known from outside.

The goal of creating "useful" vision is extremely challenging, primarily because of the intricacy of human vision, the complexity of the nerve circuitry that provides vision, and because of the potential for the body to reject implantation of a foreign object, especially near the retina, which is as delicate and complex as the rest of the brain. Creation of anything like normal vision by a prosthesis would require the ability to generate images that contain at least the attributes of spatial detail (i.e. to permit reading or other fine work), color vision and variations of contrast (which improve the resolution in an image). These qualities are normally provided by nerve cells in the center of the retina (i.e. the macula) and, as such, these attributes of vision can be considered to represent "central vision". The area of the macula, however, is only a small fraction of the total area of the retina. The majority of primate vision is actually "peripheral" vision that is designed simply to detect the presence of objects in the environment. Once alerted, a person would then move the eye so that the center of the retina (with its much higher density of nerve cells and hence greater capacity to resolve visual detail) fixates on the target of interest. Peripheral vision provides an especially good ability to detect motion because of the presence of nerve cells with relatively large receptive fields (i.e. the area within which the cells will respond to moving objects). Ideally, a visual prosthesis should be designed in a manner to permit restoration of both central and peripheral vision, depending upon the needs of individual patients. A visual prosthesis could also be used to influence light-induced circadian rhythms, modulate pupillomotor responses to control the amount of light entering the eye, or, if a prostheses were placed in homologous regions of the retina in both eyes, provide stereopsis (i.e. depth perception).

The requirements differ for a prosthesis able to generate useful central vision as compared with useful peripheral vision. The relatively high resolution of central vision can only be delivered by a prosthesis if the electrode array that abuts the retina contains a relatively high density of stimulating elements. Driving the larger number of electrodes needed for this purpose imposes greater demands upon the power delivery of the prosthesis, which must in turn obtain that power from an artificial, external source, given that the intensity of the incident light that illuminates the retina is woefully insufficient to electrically activate nerve cells (which evolved to respond with high sensitivity to light, not electricity)). The relatively intense power source required has the potential to damage the retina because of the unavoidable loss of energy at a secondary coil of a radiofrequency system that produces heat. Similarly, attempts to obtain sufficient energy from light entering the eye (as from a prosthetic device that provides electronically filtered light from the outside) also have the potential to damage the retina because of the well-described phototoxicity that would occur with the levels of light needed to power a prosthesis.

Restoring peripheral vision (i.e. mainly detection of objects in the environment) is also a challenging goal, although the challenges differ in several respects from those described above with respect to central vision. The normal range of peripheral vision equals approximately 150 degrees in each eye (90 degrees from the center to the farthest extent to the side of the head, and 60 degrees from the center toward the nose). As is known from clinical experience with patients who are going blind from retinitis pigmentosa, a patient's ability to navigate within unfamiliar environments becomes limited when the full extent of the field of peripheral vision becomes less than ten degrees of visual angle. As such, a retinal prosthetic must provide at least ten degrees of peripheral vision, and preferably much more.

There is, however, a severe barrier to achieving larger degrees of peripheral vision. Fundamentally, the ability to achieve degrees of visual field depends upon the ability to stimulate the nerve cells within an area of retina that corresponds to that area of visual field. Ten degrees of visual field corresponds to roughly 3 mm over the retinal surface. Hence an array would have to cover at least a 3×3 mm region of retina to meet the most minimal criteria for delivering an adequate degree of benefit to severely blind patients. It would be preferable to provide substantially more peripheral vision than 10 degrees, given that 150 degrees is the normal amount of vision that humans can experience. Inserting large stimulating arrays is problematic, since an incision in the wall of the eye must be at least as large as the width of the stimulating array. Larger incisions are known to be associated with greater risk for surgical complications, and hence there would seem to be a practical limit on the degree of peripheral vision that could be achieved.

Solutions to the challenges in providing a relatively large degree of peripheral vision have been proposed in the prior art. Polyimide films with embedded microelectrodes have been used for neural recording in animal experiments (25). The present inventors and their associates first taught the use of such thin and flexible microfilms for use in human retinal stimulation (See U.S. Pat. No.: 6,324,429 to Shire et al.; U.S. Pat. No. 6,120,538 to Rizzo et al. and U.S. Pat. No. 5,800,530 to Rizzo, the teachings of which are incorporated herein by reference). These microfilms can be placed into an eye through a relatively small incision in the wall of the eye. Once inside of the eye, these films can be flattened onto the retina to provide a relatively large surface area of nerve stimulation.

Another solution, also taught by the present inventors, is the use of an inflatable microelectronic device (see U.S. Pat. No. 6,368,349 to Wyatt et al., the teachings of which are incorporated herein by reference), which can also be inserted through a small incision and then expanded within the eye so that the array contacts the epi- or sub-retinal surface. Further solutions are still needed to address the issues inherent in providing large degree peripheral vision.

Prior art retinal prostheses have been created through the various choices of stimulation location (i.e. epi- vs. sub-retinal), various means of powering the device (i.e. use of light vs. radiofrequency transmission), and various locations for obtaining an image (i.e., extraocularly or intraocularly). In particular, Chow et al. have taught the use of sub- or epi-retinal devices that use light for transmission to the prosthesis of spatially specific visual detail and power. (See, for example, U.S. Pat. Nos.: 6,075,251; 6,069,365; 6,020,593; 5,949,064; 5,895,415; 5,837,995; 5,556,423; and 5,397,350). Michelson, referenced above, has taught the use of an epi-retinal device that utilizes both light and radiofrequency transmission. Subsequently, Humayun et al. taught the use of epi-retinal devices that use radiofrequency transmission alone. (See U.S. Pat. No. 5,935,155). The teachings of all of the references cited above are incorporated herein by reference.

There is therefore still a need for an improved ocular device capable of more safely and effectively performing the needed functions of a retinal prosthesis by minimizing the anatomical disruption of the delicate interior of the eye while maximizing the safe delivery of the energy needed to drive a large number of stimulating elements.

SUMMARY OF THE INVENTION

The present invention discloses an ocular device that can more safely and effectively perform all functions needed of a retinal prosthesis with electronic components that are placed outside the wall of an eye, are powered wirelessly provided by an external power source, and which provide a patient with a view determined by natural motion of the eye and triggered by natural incident light converging at the retina. In one aspect, the invention is an externally powered, light-activated, sub-retinal prosthesis in which natural light entering the eye conveys visual details to the sub-retinal prosthesis, while wireless radiofrequency transmission provides the power needed to stimulate the retina, which would be insufficient if it were obtained from the intensity of incoming light alone. In another aspect, the present invention provides means for controlling and communicating, from outside a patient's body, a transformation algorithm and parameters of the algorithm by which an optical pattern incident on the prosthesis is converted to a pattern of electrical stimulation of the retina that conveys useful information to the patient and influences visual function.

In one embodiment, the invention is a retinal prosthesis comprising an RF coil attached to the outside of and moving with an eye to receive power from an external power source. Electronic circuitry is attached to and moves with the eye and is electrically connected to the RF coil. A light sensitive array is electrically connected to the electronic circuitry and located within the eye for receiving incident light and for generating an electrical signal in response to the incident light. A stimulating array abuts a retina of the eye and is electrically connected to the electronic circuitry to stimulate retinal tissue in response to the electrical signal from the light sensitive array. In another embodiment, the present invention further comprises wireless control means for specifying, from outside a body of a patient, transformation by which electrical signals from the light-sensitive array are transformed into a set of electrical patterns to the stimulating array to influence visual function.

BRIEF DESCRIPTION OF THE DRAWING

The invention is described with reference to the several figures of the drawing, in which.

DETAILED DESCRIPTION OF THE PREFERRED EMBODIMENTS

Figure 1:
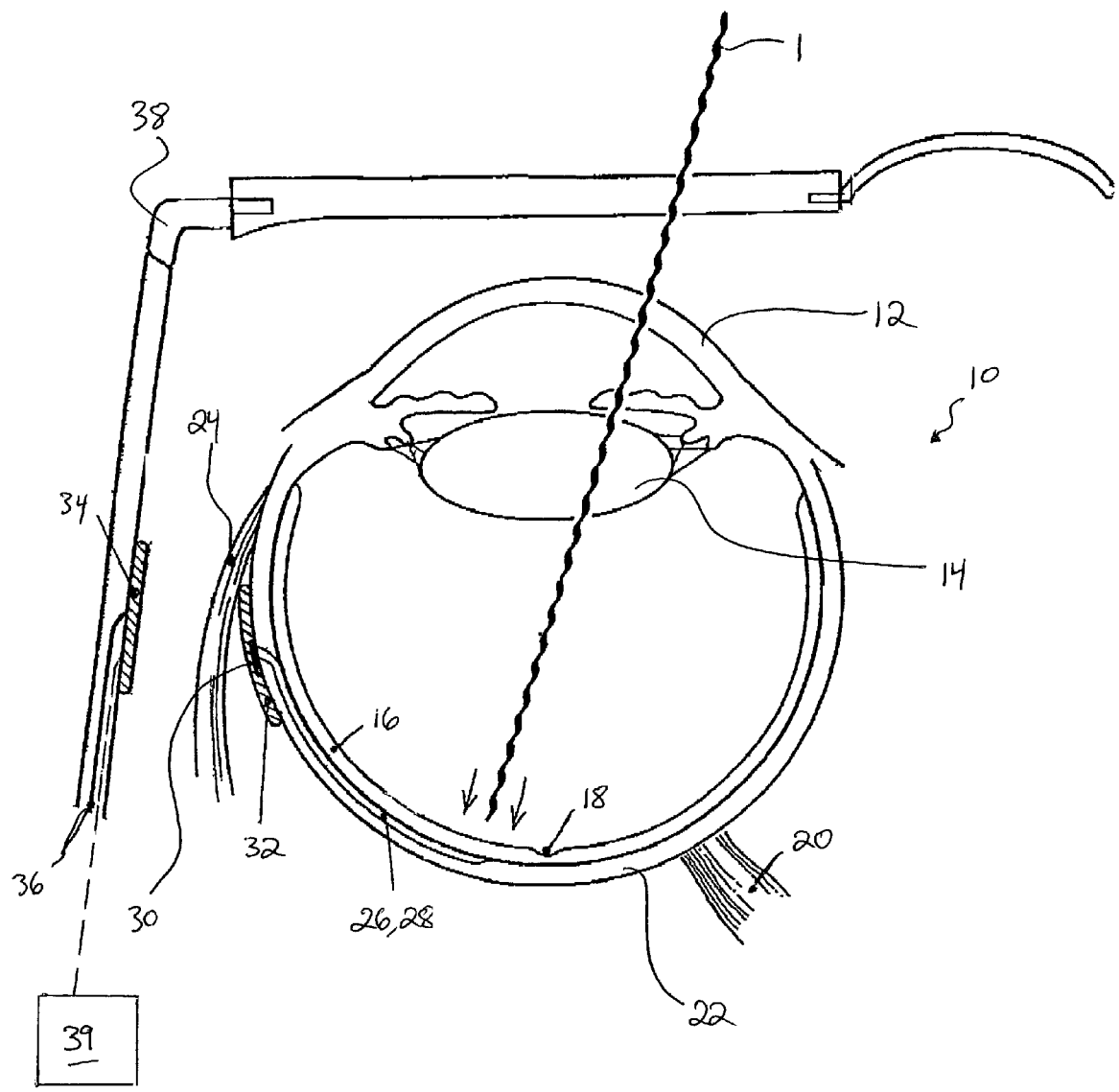
FIG. 1 is a schematic illustration of a retinal prosthesis according to one embodiment of the invention.

A retinal prosthesis is disclosed that is designed to emulate the natural workings of the eye (for instance, by using natural light entering the eye to trigger the spatial pattern of nerve stimulation) while also enhancing the biocompatibility (16, 27, 70, 103) of the device by virtue of its low profile, flexible configuration, and implantation almost entirely outside of the eye. The eye is especially prone to inflammation, which over time can be destructive and, in the worse cases, can cause loss of the eyeball. In a preferred embodiment, the present invention utilizes materials and a structure that minimizes the potential for ocular damage. In particular, this present invention seeks to alter the normal anatomy of the eye as little as possible and to remove potentially harmful mechanical and thermal (43, 87) stress from the retina, which is the most delicate element of the eye.

Enhanced biocompatibility is achieved by placing almost the entire retinal prosthesis outside of the eye. In a preferred embodiment, only an ultra-thin and flexible, light-sensitive and stimulating array is placed inside of the eye. In this configuration, more than 90% of the mass and more than 90% of the area of the device is implanted external to the eye, and preferably more than 99% of the mass and 95% of the area is so implanted. The external surface of the eye (i.e. the sclera) is made of collagen and is extremely tough, and is thus able to withstand chronic implantation of the device. This preferred embodiment also maintains a secondary RF coil outside of the eye which, given the significant power requirements of a prosthesis having a large number of stimulating elements, protects the retina from the inevitable and damaging heat generated by the secondary coil. The success of this embodiment is dependent upon use of materials that permit fabrication of a flexible prosthesis that is able to match the natural curvature of the eye. Additionally, because of its relatively low profile (a very few millimeters or even a single millimeter or less) the prosthesis will be able to move freely in the orbital space in concert with naturally occurring eye movements.

A preferred method of implantation places the prosthesis along the lateral side of the eye (i.e. the side facing the side of the skull). In this location the more delicate structures in the front of the eye (i.e. in front of Tenon's fascial layer) are largely or entirely avoided. Operating and implanting behind the Tenon's fascial layer is advantageous because this retro-orbital space (i.e. the space behind the eye) is sterile, unlike the front of the eye, and because it is filled with soft adipose tissue that is compliant and easily able to accommodate the presence of an external prosthesis. A prosthesis could not be as safely or comfortably placed further toward the front of the eye because of the potential for infection and because of interference with the more complicated external anatomy of the front of the eye (i.e. which provides a delicate and conformal layer of tissue which extends under the lids and over the front parts of the eye that are visible), among other features. The preferred embodiment includes an elongated bridge (which can be of variable length from 0.5–15 mm) that connects the secondary coil to the discrete and integrated active electronic components. This bridge exists to allow the surgeon opportunity to attach the segments containing the coil and electronics on either side of one of the extra-ocular muscles, without having to dis-insert and re-attach the muscle to attach the prosthesis to the eye. In this regard, the placement of the secondary coil over the side of the eye (rather than around the front of the eye, for instance) is particularly important since such forward placement of a coil would require dis-insertion of at least four extra-ocular muscles to achieve a deep enough placement so as to be medically acceptable (i.e. if the coil were placed in front of the muscles, the coil could extrude through the soft tissues in the front of the eye and be medically hazardous). As is widely appreciated by ophthalmologists, dis-insertion of four extra-ocular muscles at one sitting, even if they are promptly re-inserted, causes anterior segment ischemia because of an unacceptable decrease in blood delivery to the front of the eye.

A retinal prosthesis requires substantial power, which is primarily used to drive electrical pulses to the stimulating array. In the prior art, power receiving coils have been placed inside of the eye but far from the retina in an intraocular platform located just behind the iris. (See, for example, U.S. Pat. Nos. 6,120,538 and 5,800,530, referenced above). In a preferred embodiment of the present invention, the secondary receiving coil is placed outside of the eye. This external position takes advantage of the dense sclera and the high volume blood flow of the choriocapillaris to shield the retina from any significant heating. In this preferred embodiment, the secondary coil is positioned on the lateral side of the eye (i.e. facing the temporal region of the skull), where power transfer from a primary coil attached to the frame of a pair of glasses (or even placed under the skin, where it would be protected and perhaps more cosmetically acceptable, as is done with cochlear prosthetics) would be facilitated by the relatively close apposition of the two coils. The secondary receiving coil is integrated with the remainder of the prosthesis in a monolithic fashion and includes a mostly microfilm structure (made of polyimide or parylene, for instance) which is flexible. This flexibility permits the surgeon to attach the device to the outside of the eye where the prosthesis is able to match the contour of the eye, which permits the implanted structure to rotate in kind with the natural movements of the eye.

A novel solution to the problem of providing stimulation to a relatively large area of retina so as to restore vision to a large area of the visual field is the use of a flexible, wide-field stimulating electrode array and the necessary surgical methods to implant the array. A novel surgical method teaches the creation of a large (greater than ¼ circumference) region of retinal detachment by cutting the attachment of the peripheral retina from the underlying or a serrata. Modern intraocular surgical methods permit a controlled retinal separation (including up to 360 degrees). Once created, a very large electrode array (e.g. with a surface area of roughly 100 mm$^2$ area, or greater, with potentially thousands of electrodes) can be placed under the retina, which would then be re-attached by standard surgical means. (A wide-field stimulating array of this type could also be placed over the epi-retinal surface, in which case the retina would not be detached but the vitreous humor of the eye would be removed by standard surgical techniques). The wide-field, sub-retinal electrode array would be fixed in position simply by virtue of its placement within the sub-retinal space (i.e. between the retina and retinal pigment epithelium). The wide-field, sub-retinal electrode array could be constructed to be porous (perhaps with thousands of pores), mesh-like (to facilitate diffusion of ions, nutrients, cellular waste, and other biochemical compounds between the retina and the pigment epithelium, as normally occurs) or fimbriated (i.e. having a large number of thin, flexible extensions each having an electrode which is connected by a microwire to a central pod that contains a demultiplexor—these numerous fimbria could be pre-operatively imbedded in an ultra-thin, pliable, biodegradable substrate, like an agar, which would allow the composite structure to be rolled into an elongated shape to pass through a small opening in the eye, wherein the composite structure could be unrolled to stimulate a wide array of neural tissue). A wide-field, epi-retinal electrode array would require a means of attachment to the retina, which can be achieved with microtacks (140), adhesives, compression by silicone oil filling the vitreous chamber, biologically active compounds that generate local reactions of tissue to cause adhesion (with or without the use of intraocular gas), or other means.

A wide-field stimulating array, which could exist as an integral component of a preferred embodiment of the retinal prosthesis described herein, would also contain intrinsic microcircuitry, including but not limited to, photodiodes or other light responsive elements, radiofrequency coils to receive power and visual signal, and one or more demultiplexors. The connecting wires to each of the large number of electrodes contained on the wide-field array would produce an impractically thick cable, which would not be conducive to chronic use in the eye since that cable must penetrate the wall of the eye to connect to external electronics. As such, one or more demultiplexors can be used to receive signals from a small number of incoming wires and then issue stimulus commands to an large number of stimulating electrodes. The intrinsic microcircuitry contained with the wide-field stimulating array could also contain custom microcircuitry that could provide: 1) stimulus control in a manner that mimics natural retinal function; 2) stimulation that creates center-surround neural responses; 3) spatial filtering; 4) stimuli that generate retinal responses like those influenced by natural light-dark adaptation; 5) algorithmic commands as received from external sources; 6) stimuli that track movement of objects with the visual environment; 7) reverse telemetry of hardware and biological function, including but not limited to electrode resistance, temperature, pH, neural activity, presence neurotransmitters or other biochemicals; and 8) and other functions that would either contribute to creation of vision or monitor the safety or effectiveness of the implanted device.

The wide-field array, especially with imbedded, active microcircuitry, would need to be made of or coated with material(s) that provided hermetic encapsulation (80, 97–103) to protect the microcircuitry from the destructive effects of bodily fluids, particularly sodium and potassium ions. The wide-field stimulating array could also contain higher and lower density regions of stimulating elements to more closely resemble the natural architecture of the receptive fields of the retinal nerve cells, which vary considerably with respect to the eccentricity of the cells within the retina. For example, the peripheral retina is composed of larger cells that are arranged in populations of lower density than those found in the central retina. This architecture, as well as other features, makes the peripheral retina proficient in detection of objects, especially moving objects, within the visual environment. In a preferred embodiment, the wide-field stimulating array is made of flexible components including imbedded microcircuitry, hermetic sealing, various sizes and densities of stimulating elements and the surgical methods needed to implant through relatively small openings in the wall of the eye.

Referring now to the figures of the drawing, the figures constitute a part of this specification and illustrate exemplary embodiments of the invention. It is to be understood that in some instances various aspects of the invention may be shown exaggerated or enlarged to facilitate an understanding of the invention.

FIG. 1 is a schematic illustration of a retinal prosthesis according to one embodiment of the invention. Incident light rays 1 enter an eye 10 through a cornea 12 and crystalline lens 14 and strike a retina 16. A prosthesis, as described below, is attached to the exterior wall of the eye 10 on the temporal side (i.e., the side away from the nose). One example of the positioning of the prosthesis is shown with respect to the fovea 18 which is located at the center of the retina 16, near the optic nerve 20. The prosthesis comprises a component on which both retinal stimulating 26 and light-sensitive 28 elements are arrayed, which is inserted through an ab externo incision through the outer wall of the eye, the sclera 22, near the back of the eye 10, so that the active components of the array element abut the under surface of the retina 16. In a preferred embodiment, the retinal stimulating 26 and light-sensitive 28 elements are arrayed either near the end or along the length of the component. Examples of prior art retinal stimulation arrays are disclosed in references (13, 62, 67, 68, 73–75, 78, 82) and prior art light-sensitive arrays are disclosed in references (120,121, 128–130).

In a preferred embodiment, the retinal stimulating array elements 26 and light-sensitive array elements 28 are interlaced together in a grid-like pattern on a single array component. In one embodiment, the stimulating array elements 26 comprise electrodes, preferably including microelectrodes, and the light-sensitive array elements 28 comprise photodiodes forming an electrode-photodiode array 26, 28. In another embodiment, all electronics of the prosthesis positioned within the eye contact the retina only in a region defined by a surface area of the retina 16 covered by the stimulating array 26 (or retina stimulating/light-sensitive array 26, 28). In another embodiment, the electronic components of the prosthesis in contact with the exterior of the eye are attached so as to conform to the eye's curvature, as shown. The insertion site and the array site can be aligned nearly over one another, so as to minimize the extent of retina in contact with the foreign object.

An exterior RF primary coil 34 is mounted on the side of a pair of eyeglasses 38 (or on a similarly placed supporting structure, or, in an alternate embodiment, under the skin) near and parallel to an implanted RF secondary coil 32 so that electromagnetic fields from the former easily reach the latter to enable more efficient transmission from the primary coil 34 to the secondary coil 32. Examples of prior art coils are disclosed in references (54–57). The primary coil 34 is driven by an external transmitter circuit (not shown), carried by the patient in a convenient location such as a pocket, along with batteries to power the transmitter. The transmitter is attached to the primary coil via a cable 36. Light from scenes in the external world passing through the portion of retina immediately above the array 26, 28 is converted to an electrical signal representation of that scene by the photodiodes and conveyed by wires to a stimulator chip or other electronic circuitry 30 located outside of the eye. The electronic circuitry 30 produces a set of electrical patterns in response to the electrical signal that is conveyed by wires back to the microelectrodes in the stimulating array 26 to stimulate approximately the same portion of retina 16 through which the incident light had passed. Examples of prior art stimulator chips are disclosed in references (42, 44, 46–48, 69, 72). In one embodiment, the secondary RF coil 32 that receives power from the primary coil 34 delivers only power to the electronic circuitry 30 and no image information or information to govern the transformation of optical input to retinal stimulation is delivered.

In this design, the entire implanted portion of the prosthesis lies in a sterile region of the body entirely under the conjunctiva, minimizing the likelihood of infection of the eye through the chronic ab externo incision. The majority of the mass of the implanted prosthesis lies on the exterior of the eye and is contained in the eye socket, which is filled with fat and thus sufficiently compliant to allow for an implant thickness of one or several millimeters without resulting in mechanical damage to tissue. Furthermore, in this embodiment, the majority of the heat dissipation from the electronics also occurs outside the eye. This design thus protects the delicate retina from both thermal and mechanical sources of stress.

In another embodiment, the present invention further includes a method and control mechanism 39 for specifying and communicating, from outside a body of a patient, transformation by which electrical signals from the light-sensitive array are transformed into a set of electrical patterns to the stimulating array to influence visual function. One or more primary coils 34 serve as devices for the wireless communication of one or more transformation algorithms and parameters of the algorithms by which the optical pattern incident on the photodiode array is converted to a pattern of electrical stimulation of the retina that conveys useful information to the patient and influences visual function. Alteration of the transformation algorithm may be based on inputs from a patient (i.e. tuning) or alternatively may be based on known medical specifications promulgated to doctors and researchers.

Figure 2A:
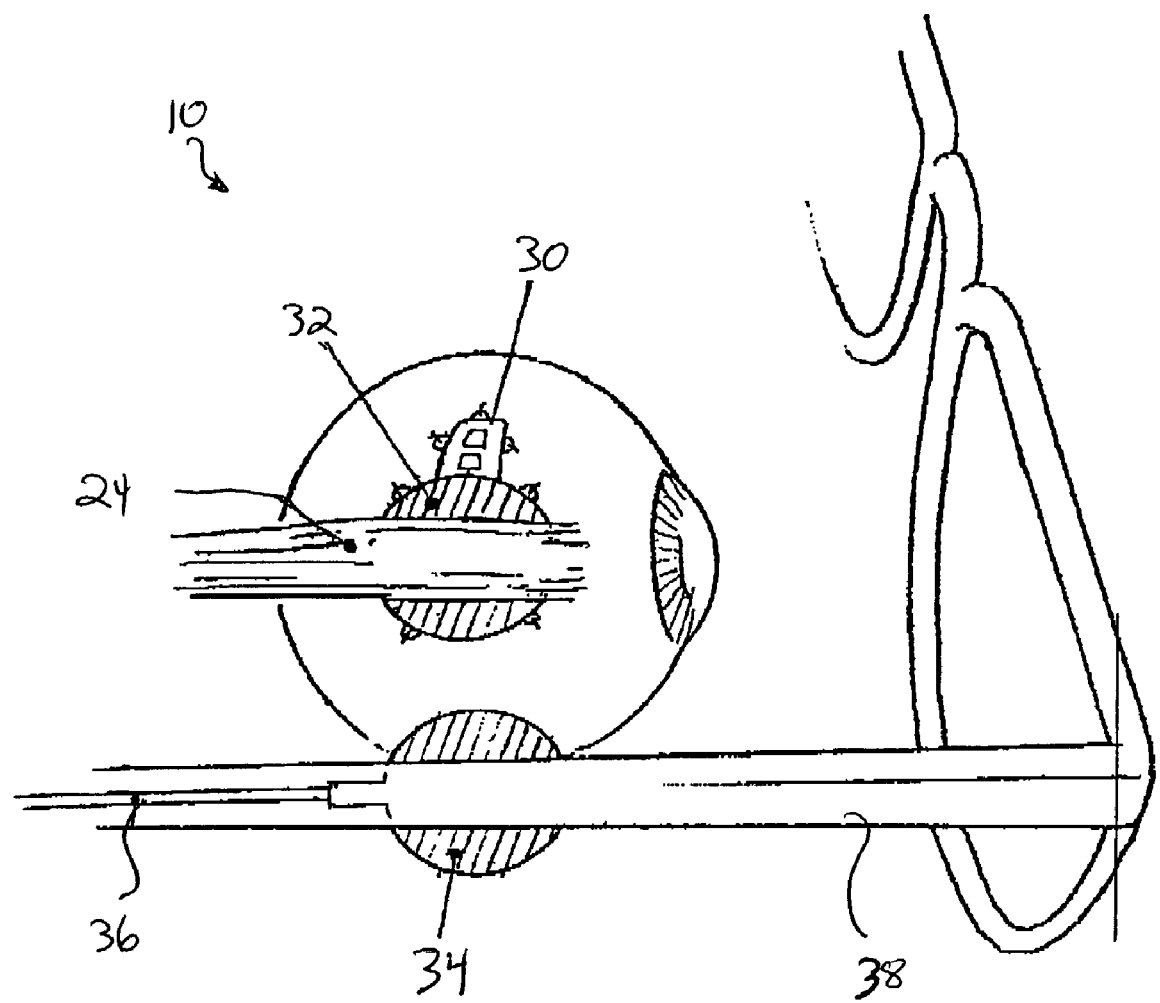
FIGS. 2A and 2B are perspective illustrations of a retinal prosthesis according to one embodiment of the invention with the extraocular muscle shown in place and reflected.
Figure 2B:
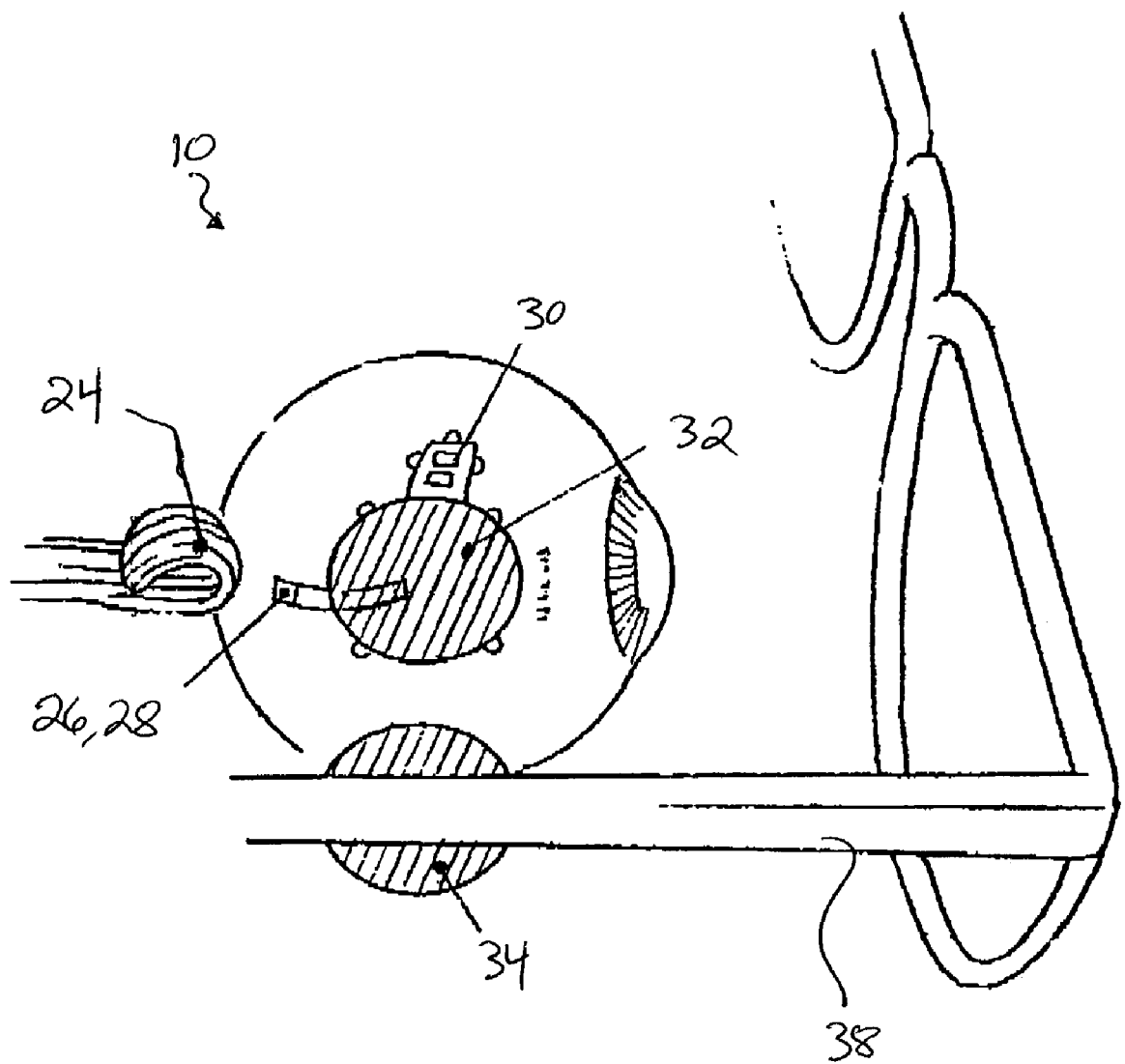

FIGS. 2A and 2B are perspective views of the placement of implanted and external components of the prosthesis according to one embodiment of the invention. FIG. 2A shows an extraocular muscle 24 in place for moving the eye, while FIG. 2B shows the extraocular muscle 24 reflected (i.e. pulled back) revealing the stimulating and light-sensitive array 26, 28, that are inserted through a small incision (or flap), both of which can be sutured closed after insertion. The thinness of the array requires only a slit-like opening in the wall of the eye which is then readily sealed by natural tissue reactions which protect against infection.

Figure 3:
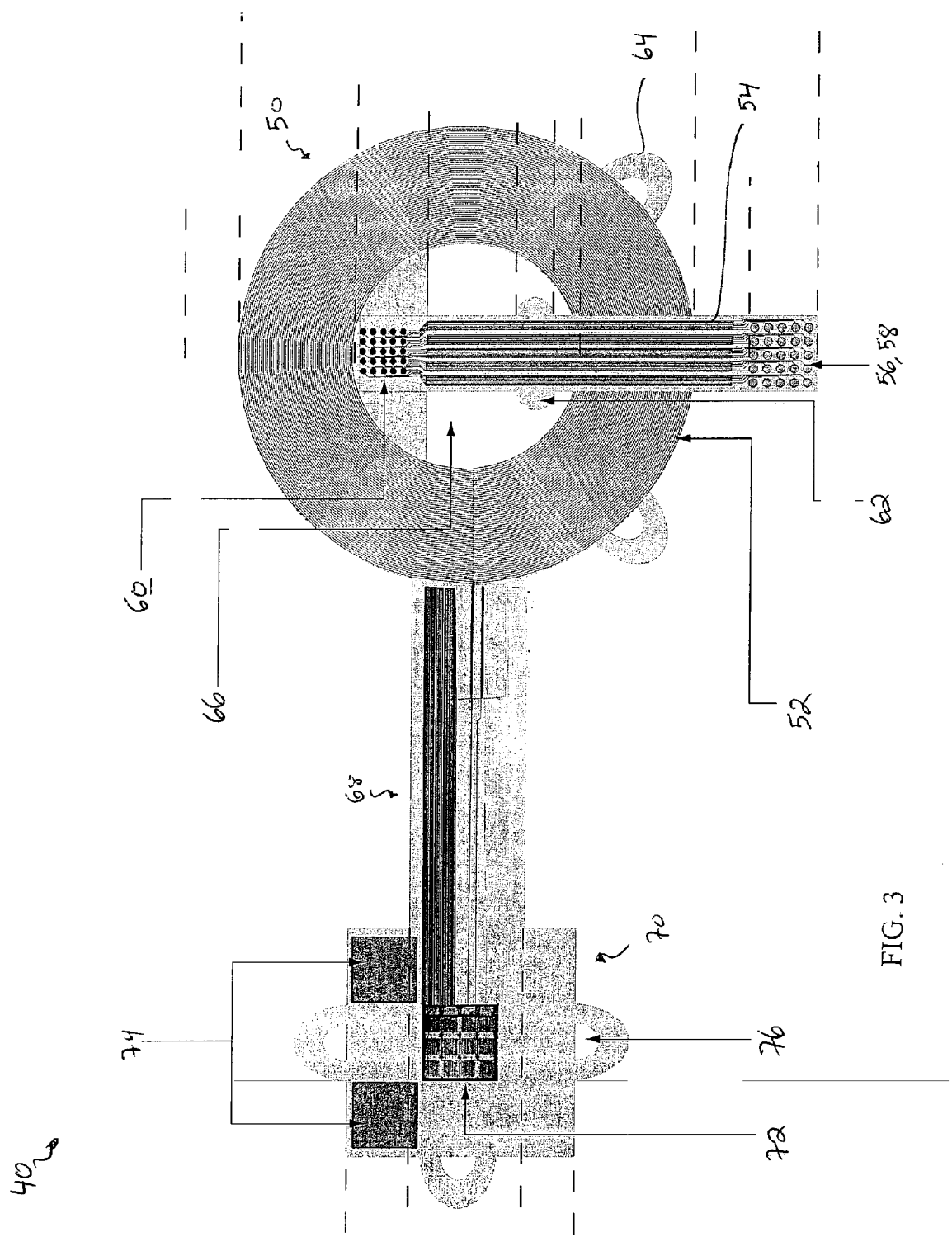
FIG. 3 is a cross-sectional view of a structure for neural tissue stimulation according to one embodiment of the invention.

FIG. 3 is a cross-sectional view of one embodiment of the invention illustrating a integrated neural tissue stimulation structure 40 having a unibody construction. The structure 40 must be tested in experimental animals before use with human patients, and the dimensions provided below are approximately appropriate for experimental implantation in a pig; however, these dimensions approximate those needed for implantation in a human.

The neural tissue stimulation structure 40 comprises three modules that are flexibly connected: a coil and array module 50, a connection module 68, and a control module 70. The coil and array module 50 comprises an RF power coil 52 for receiving power from a power source, and an array on which electrodes 56 and photodiodes 58 are integrated in a grid-like pattern. The electrode array/photodiode array 56, 58 is flexibly attached to the power coil 52 by a flexible wire connection bus 54 that is connected to the power coil via the bonding attachment area 60. The flexible wire connection bus 54 has surgical handles 62 and the power coil has surgical handles and/or holes 64 for manipulation of the prosthesis by the surgeon. The design allows for surgical access space 66 within the power coil 52. Photodiodes on the photodiode array 58 are the input devices for optical signal to the prosthesis 40, and microelectrodes on the electrode array 56 are the output devices through which current is passed to the retina to stimulate it and thereby convey useful visual information to the patient. In a preferred embodiment, the electrode-photodiode array 56, 58 measures 2 mm in length and the power coil 52 has an inner diameter of 6 mm and an outer diameter of 12 mm. The flexible wire connection bus 54, from attachment area 60 to array 56, 58, measures 10 mm in length. All of these components are ultra-thin, having a height preferably less than 1 mm.

The connection module 68 comprises a flexible bridge for sending the electrical signals to and from a stimulator chip. The connection module is thin and smooth and of a length such that it may be positioned underneath an extraocular muscle for moving the eye without negatively affecting operation of the muscle. In a preferred embodiment, the connection module measures 9 mm in length and 3 mm in width.

The control module 70 comprises a stimulator chip or other electronic circuitry 72 for receiving input signals from the photodiode array components 58 and controlling the electrical signals delivered to the electrode array elements 56 for retinal tissue stimulation. The stimulator chip 72 contains rectifier circuitry to rectify the oscillating voltage obtained from the power coil 52, and the control module 70 further comprises discrete power supply capacitors 74 for smoothing the rectified voltage and delivering it to the stimulator chip. As a result of the substantial currents required for each electrode to reach perceptual threshold in blind human subjects (at least 350 microamperes for 400 micron diameter electrodes with 1 millisecond pulses in our own experiments), the filter capacitors will be quite physically large, preferably several microfarads, if a number of electrodes are to be driven at once. Such large capacitances cannot be readily obtained on a chip, which therefore requires the use of these separate discrete devices. In this embodiment, signal information for the conversion parameters of the transformation algorithm is also received by the power coil 52 and delivered to the stimulator chip 72. In an alternate embodiment the rectification is done more efficiently by discrete Schottky diodes also located in the control module 70. In a preferred embodiment, the control module has dimensions of 6 mm in length and width.

Optical communication from the external world is wireless in this invention, as it is in the normal functioning of a healthy eye. The RF secondary coil 52 is the input device for transmission of power to the prosthesis by magnetic coupling from the RF primary coil outside the body. Electrical power from the RF secondary coil 52 electrical signals from the photodiodes 58 are sent to the stimulator chip 72 through a set of embedded wires. The stimulator chip 72 receives transformation information from the RF secondary coil 52 through the same set of wires that carry power. The stimulator chip 72 processes the data from the photodiode array 58 in accordance with a transformation algorithm and uses this information to apply current pulses to the microelectrodes 56 to stimulate the retina in a pattern that conveys to the patient useful visual information. In this embodiment, the RF secondary coil 52 also serves as the input device for the communication of a transformation algorithm and parameters of the algorithm by which the optical pattern incident on the photodiode array is converted to a pattern of electrical stimulation of the retina that conveys useful information to the patient and influences visual function.

In other embodiments, retinal stimulation could be achieved through chemical means by the controlled release of neurotransmitters, neuromodulatory agents, or ionic species from the output portion of the array. The operation of a system utilizing chemical stimulation means operates in a similar manner to that described above; however, in this embodiment, the electronic circuitry supplies an electrical signal to the stimulation array which activates the chemical release mechanisms on the stimulation array (which would require a microfluidic or other device and a reservoir to deliver the chemicals over a prolonged period of time).

Figure 4:
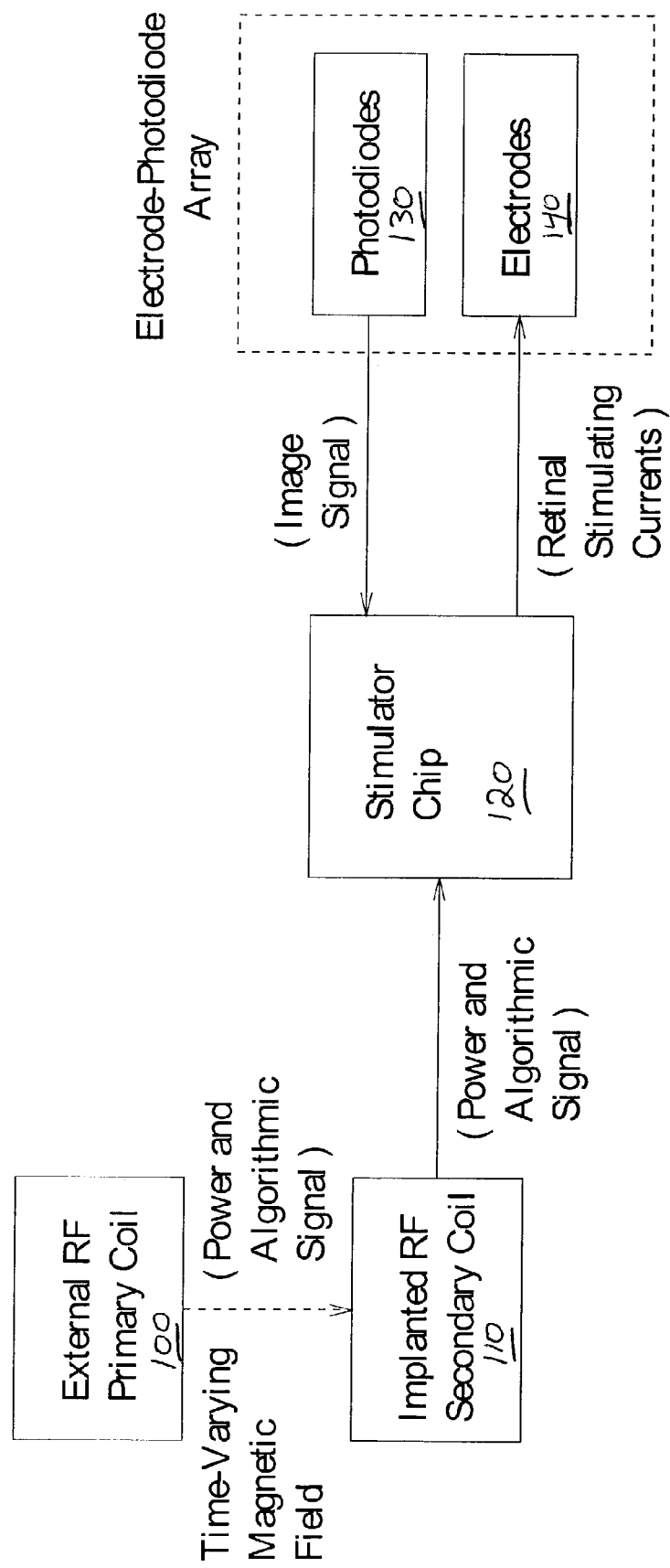
FIG. 4 is a systems diagram illustrating the flow of information and power between subsystems of a neural tissue stimulation structure without a data coil according to the embodiment of the invention shown in FIG. 3.

FIG. 4 is a systems diagram illustrating the flow of information and power between subsystems of a neural tissue stimulation structure without a separate coil for the transformation data, according to the embodiment of the invention shown in FIG. 3. Wired connections are represented by solid arrows and magnetic field linkages are represented by dashed arrows. By means of a time-varying magnetic field, an external RF primary coil 100 wirelessly supplies power and a signal for information conversion parameters for the transformation algorithm to an implanted RF secondary coil 110. The power and transformation signal are delivered to the stimulator chip 120. The stimulator chip receives an image signal from the photodiode array 130 and delivers retinal stimulation currents to the electrode array 140 as controlled by the transformation algorithm.

Figure 5:
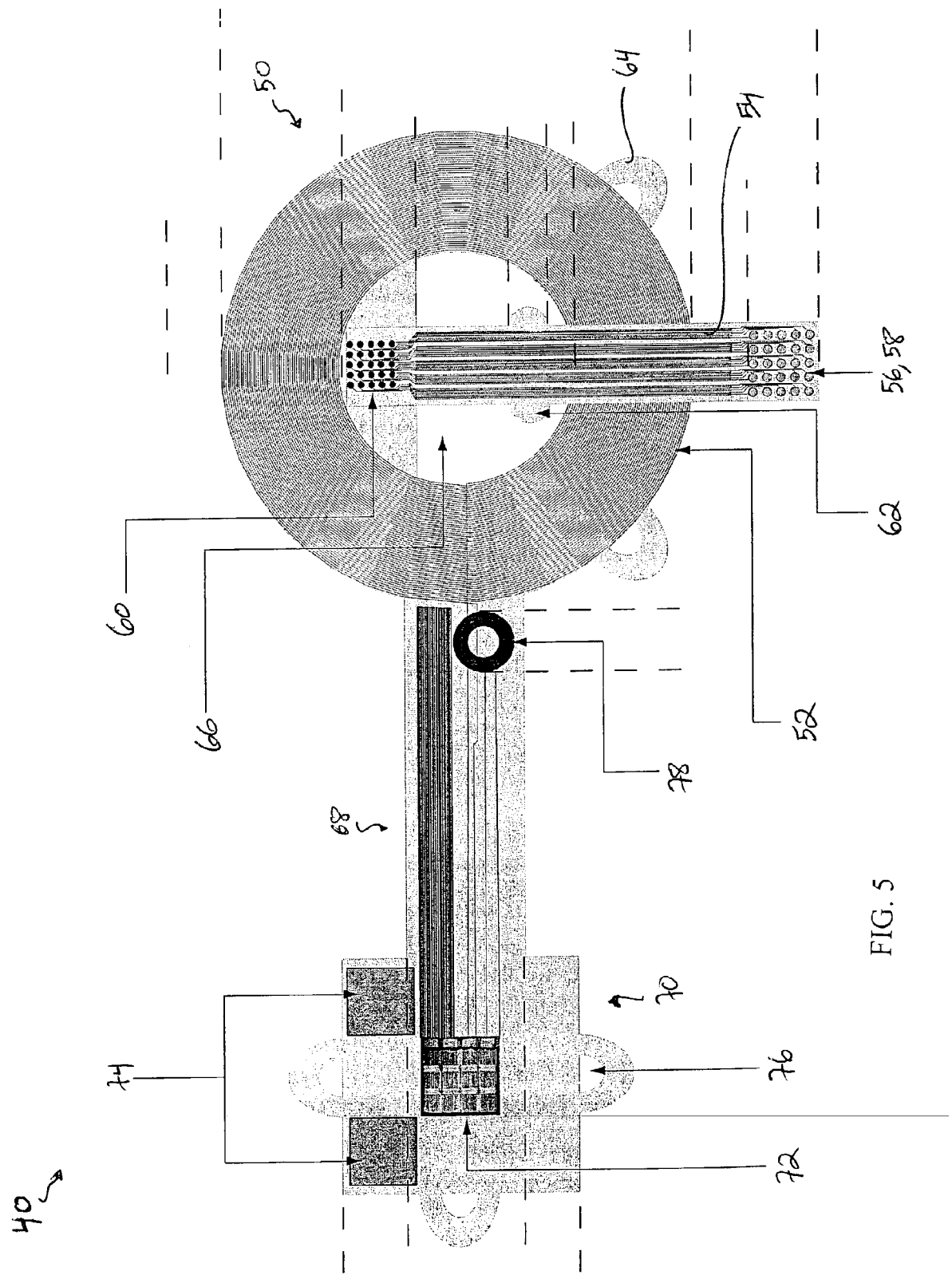
FIG. 5 is a cross-sectional view of a structure for neural tissue stimulation with data coil shown according to one embodiment of the invention.

In the embodiment shown in FIG. 5, the elements are the same as those described above with respect to FIG. 3, except that instead of the stimulator chip 72 receiving transformation information from the RF secondary coil 52 through the same set of wires that carry power, the transformation information reaches the stimulator chip 72 through embedded wires from a separate RF data secondary coil 78, allowing power and transformation information to be communicated through separate channels. In a preferred embodiment, the data coil 78 has an outer diameter of 2 mm. This alternate design has the advantages of removing the somewhat complex and frequently power-inefficient circuitry needed to modulate the transmitted power and of allowing the transformation information to be received on a physically separate coil that is less subject to interference arising from the large amplitude power transmission. The disadvantage is the need for entirely separate, but much lower power, data transmission and reception circuitry. With or without the data coil, the transmission of both power and transformation information is wireless in the sense that no wires run from the implant to any external device lying outside the eye socket.

The external RF primary coil and the implanted RF secondary coil are designed so that a periodic (typically sinusoidal) current drive to the primary coil creates a time varying magnetic field which passes through the RF secondary coil and thereby induces a voltage which is used to provide RF power to the stimulator chip and other electronic circuitry. To communicate or update the algorithm for transforming the image input to stimulating array output, the current drive to the primary is modulated in amplitude or frequency to convey information.

Figure 6:
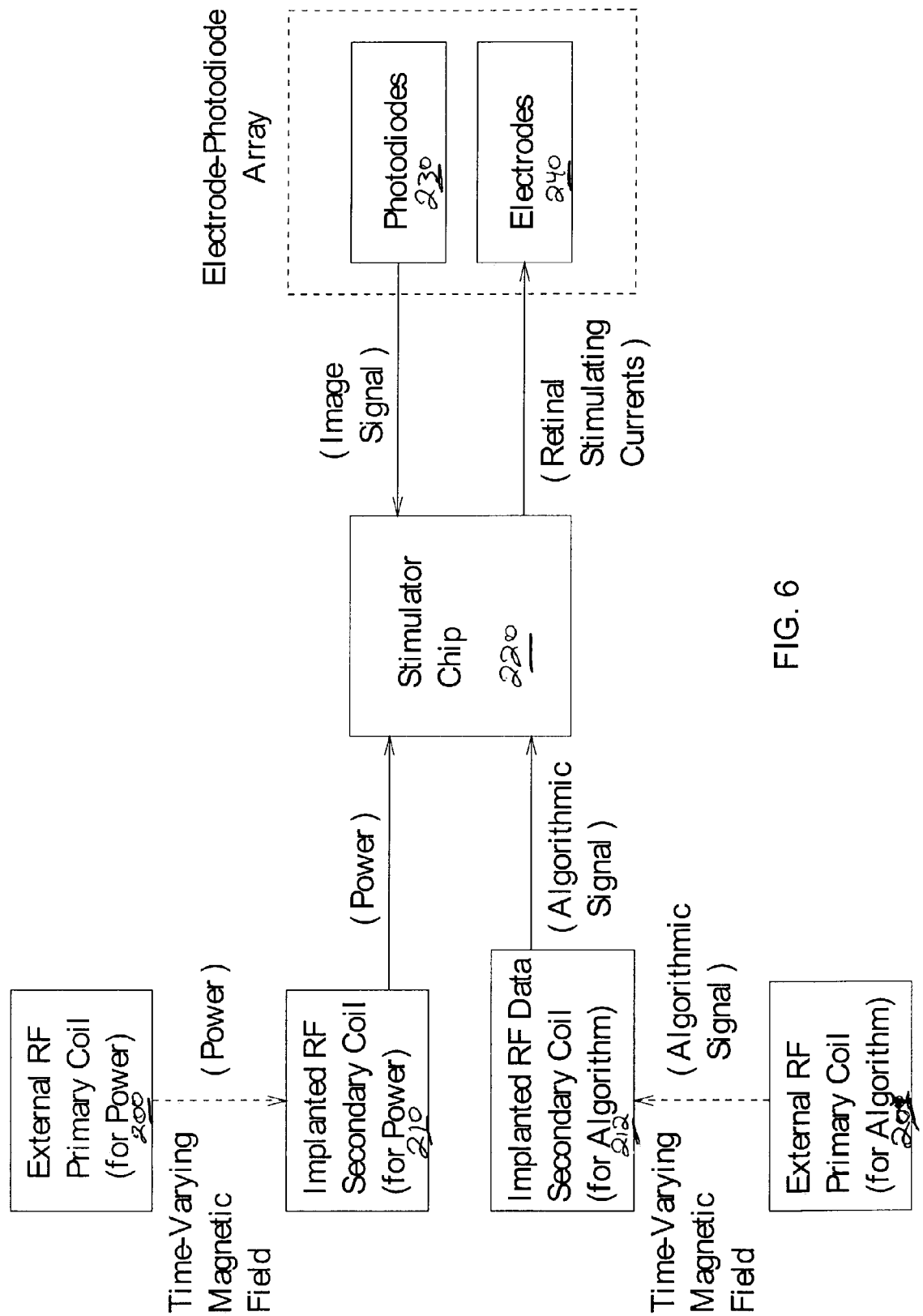
FIG. 6 is a systems diagram illustrating the flow of information and power between subsystems of a neural tissue stimulation structure with a data coil according to the embodiment of the invention shown in FIG. 5.

FIG. 6 is a systems diagram illustrating the flow of information and power between subsystems of a neural tissue stimulation structure with a data coil according to the embodiment of the invention shown in FIG. 5. By means of a time-varying magnetic field, one external RF primary coil 200 wirelessly supplies power and another external primary coil 201 supplies the signal for information conversion parameters for the transformation algorithm The power is delivered to the implanted RF secondary power coil 210, while the transformation algorithmic signal is delivered to an implanted RF data secondary coil 212. Power delivered by the RF secondary power coil and the transformation algorithmic signal delivered by the RF secondary data coil are received by the stimulator chip 220. The stimulator chip receives an image signal from the photodiode array 230 and delivers retinal stimulation currents to the electrode array 240 as controlled by the transformation algorithm.

In a preferred embodiment of the system illustrated in FIG. 6, power will be transmitted to the implanted RF secondary power coil at a frequency of 125 KHz and the transformation signal will be transmitted at a frequency of 13.56 MHz. The frequencies 13.56 MHz and 125 KHz are among those allowed by the FCC for Industry, Scientific, and Medical (ISM) use. ISM applications are allowed, subject to field strength limits, in any band over 9 KHz except those prohibited in FCC Code 47 part 18.303. The 13.56 MHz frequency is one of those allocated specifically for ISM under part 18.301.

Power is delivered at the lower frequency of 125 KHz for a number of reasons. Current crowding and skin depth effects in the wires of the secondary coil increase with frequency. These effects increase the effective resistance of the wires, and therefore power consumption and the resulting production of heat. Parasitic capacitances in the coil may also yield negative effects at high frequencies, exciting resonances which serve only to burn power in the parasitic resistances. In addition, using a lower frequency allows the use of synchronous rectifiers controlled by comparator circuits. At higher frequencies, these circuits would use too much overhead power to be useful.

Improved biocompability of the prosthesis is achieved by creating a sufficiently thin, flexible, waterproof device. In order for an implantable portion of the prosthesis 40 illustrated in FIGS. 3 and 5 to function as required, microfabrication techniques are essential for its construction. The methods of attaching the silicon integrated circuit to the flexible substrate containing the interconnection wiring are described below. In one embodiment, the integrated circuit has solder bumps evaporated onto its bonding pad surfaces using a photolithographic masking process. The bumped die is then flipped over and soldered to the flexible substrate by reflowing the solder, briefly heating the assembly above the eutectic temperature of the solder mixture chosen. This same procedure may also be applied to leadless discrete components such as Schottky diodes.

In an alternate embodiment, the integrated circuit and/or discrete components may be attached to the flexible substrate using a stud bumping process. This procedure involves first compressing a gold ball onto the surface of each of the bonding pads of the circuit and/or component using a wire bonder. The wire is sheared off just above the bond, leaving a gold ball behind. This ball is then coated in conductive epoxy by dipping the bumped die into the epoxy paste, then the coated bumps are compressed in place onto the flexible circuit. The final step involves an oven cure of the completed assembly to set the epoxy and cure the optional non-conducting under-fill adhesive which may be used to further hold components in place.

The discrete chip capacitors which are part of the power supply circuit may be assembled to the remainder of the circuit in one of two ways. If soldering is to be used for the remainder of the components, conventional pre-tinned ceramic chip capacitors (e.g., Panasonic ECJ series) may be soldered to the flexible circuit together with the other components. An alternate embodiment is to use conductive epoxy to attach these components to the substrate, oven-curing the epoxy as above.

The flexible substrate itself is made in one possible embodiment as follows. A supporting silicon substrate has a polyimide layer (e.g., HD Microsystems PI-2611) spun onto its surface and cured. The copper or chrome/gold conducting layer is then added and patterned using wet chemical etching or a photoresist lift-off process. Next, a second polyimide layer is spun on, and the regions where circuit components are to be added are exposed by selective dry etching or laser ablation of the upper polyimide layer in the desired areas. Finally, the completed components are removed from their supporting substrate. The stimulating electrode arrays may be fabricated in an identical manner, only the stimulating electrode surface material used in that case is activated iridium oxide. In an alternate embodiment of the flexible circuit fabrication technique, pre-fabricated polyimide sheets may be used, as in conventional thick film circuit manufacturing;

Since polyimide is not resistant to the incursion of bodily fluids over long periods of time and because salty body fluids are destruction to electronic components, an additional layer of encapsulant material is required. Rather than encapsulating polyimide in yet another material, in an alternate embodiment of the flexible circuit encapsulation technique, the spun-on polyimide films in the above may be substituted by any of the following more impermeable films: layers of parylene may be vapor-deposited onto the host substrate using a room temperature CVD process; medical-grade silicone films may be spun onto the host substrate and oven-cured; or superhydrophobic, Teflon-like fluorocarbon films deposited by spin coating or plasma enhanced chemical vapor deposition may also be used. By using one of these latter or similar films, a single material can serve as both electronic insulator for the microelectronics and hermetic encapsulant. Use of one rather than two or more materials that would need to be effectively bonded to one another significantly simplifies the manufacture of such device and improves reliability of the process.

It is relevant that the most promising patients for a retinal implant are almost surely those who have had normal vision at one time in their lives. Absent normal vision in childhood, the visual cortex of the brain does not to develop normally for processing retinal input. However, the stimulating array provides an extremely unnatural form of neural stimulation to the retina, resulting in a pattern of neural pulses traveling down the optic nerve to the brain that are unlike those to which the brain adapted during childhood. Furthermore, the precise relation between the impulse patterns in the optic nerve and the image those patterns convey to a healthy human is still a very active research area with many issues not yet resolved.

An additional problem is that no practical method is known for determining in a patient precisely what type or health of neurons that lie under or in proximity beneath each electrode or of determining how each specific neuron in a patient responds to the unnatural electrical stimulation an electrode provides. (34, 37, 38, 62, 82). Furthermore, the combined effects of stimulation through a collection of nearby electrodes in an array is not well understood.

In light of these problems and unknowns, it is likely that for a substantial period of time the only practical approach will be to perform retinal stimulation experiments with implanted prostheses by intermittant changes in the functioning of the algorithm (in distinction to the real-time control of the processing of these images) to vary the transformation from incoming image to electrical stimulation in response to patients' reported perceptions. Examples of prior art retinal adjustment methods are disclosed in references (30–33, 35, 36, 39, 41). The information gained is then used to alter and improve the transformation algorithm to improve its ability to transmit useful information. The best transformation or algorithm is likely to vary from one patient to another and also over time with aging or the progression of the disease. The ability to conveniently and safely alter from outside the body the transformation method by which images are transformed or encoded as electrical stimulation patterns is a significant improvement offered by this invention over existing designs for retinal prostheses. Communicating and altering this transformation by RF requires extremely low bandwidth compared with transmission of visual data, since the transformation would normally remain unaltered for long periods, from minutes to weeks or perhaps longer, in contrast to the much higher bandwidth required to convey a continuous moving image of the rapidly changing visual world we observe. Eventually, perhaps, medical standards will be developed to allow a prosthesis to function with pre-determined transformation parameters. It is envisioned that testing sessions with patients will allow communication of the quality of visual images which will provide information used to alter stimulation algorithms which are then wirelessly transmitted to the implanted device. In this way a highly versatile stimulator can be achieved without the need for replacing the implanted hardware.

In an alternative embodiment, a neural stimulator according to the present invention may be used to stimulate neural tissue other than the retina. For example, a wireless, chronically implantable neural tissue stimulator may be implanted elsewhere along the visual pathway, including the optic nerve, primary visual cortex, secondary visual cortices, chiasm, the optic tract, lateral geniculate body, and optic radiations. Other areas of the body suitable for implantation of a neural stimulator according to the present invention include but are not limited to the auditory pathway, the spinal cord, the diaphragm and nerves to the diaphragm, nerve regulating bladder and bowel function, and peripheral nerves. In these various embodiments, the photodiode array is replaced with a different sort of array that delivers an input signal to the stimulator chip to provide the necessary electrical patterns to the electrode array for stimulation of the particular neural tissue, or alternatively input information may be wirelessly provided from a data source.

REFERENCES

Neural Coding (eye)
(1) Humayun, M., E. de Juan, G. Dagnelie, R. Greenberg, R. Propst, and H. Philips, "Visual perception elicited by electrical stimulation of retina in blind human," Arch. Ophthalmology, vol. 114, pp. 40–46, 1996.
(2) Humayun, M., E. de Juan Jr., J. Weiland, G. Dagnelie, S. Katona, R. Greenberg, and S. Suzuki, "Pattern electrical stimulation of the human retina," Vision Res., vol. 39, pp. 2569–2576, 1999.
(3) Greenberg, R., "Analysis of electrical stimulation of the vertebrate retina—Work toward a retinal prosthesis," Ph.D. Dissertation, The Johns Hopkins University, Baltimore, Md., 1998.
(4) G. S. Brindley and W. S. Lewin, "The sensations produced by electrical stimulation of the visual cortex," *J Physiol. (Lond)*, vol. 196, pp. 479–493, 1968.
(5) J. C. Lilly, J. R. Hughes, E. C. Alvord Jr., and T. W. Galkin, "Brief, noninjurious electric waveform for stimulation of the brain," *Science*, vol. 121, pp. 468–469, 1955.
(6) R. J. Greenberg, T. J. Velte, M. S. Humayun, G. N. Scarlatis, and E. de Juan Jr., "A computational model of electrical stimulation of the retinal ganglion cell," *IEEE Trans. Biomed. Eng.*, vol. 46, pp. 505–514, May 1999.

Neural Coding (Cohlear)
(7) G. M. Clark, "Electrical stimulation of the auditory nerve: the coding of frequency, the perception of pitch and the development of cochlear implant speech processing strategies for profoundly deaf people," *Clin. Exp. Pharmacol Physiol.*, vol. 23, pp. 766–776, 1996.
(8) C. Q. Huang, R. K. Shepherd, P. M. Carter, P. M. Seligman, and B. Tabor, "Electrical stimulation of the auditory nerve: direct current measurement in vivo," *IEEE Trans. Biomed. Eng.*, vol. 46, pp. 461–470, April 1999.
(9) C. Q. Huang, R. K. Shepherd, and P. M. Carter, "Electrical stimulation of the auditory nerve: pH changes in vivo and in vitro," in *Proc. 20$^{th}$ Aust. Neurosci. Soc.*, vol. 11, 2000, p. 216.
(10) B. S. Wilson, C. C. Finley, D. T. Lawson, R. D. Wolford, D. K. Eddington, and W. M. Rabinowitz, "Better speech recognition with cochlear implants," *Nature*, vol. 352, no. 6332, pp. 236–238, July 1991.

Animal Experiments
(11) Stett, A., W. Barth, H. Haemmerle, and E. Zrenner, "Network activity of the chicken retina electrically evoked by distally applied spatial voltage patterns," 26th Göttingen Neurobiology Conference, Georg-Thieme-Verlag, 1998.
(12) Stett, A., K. Kohler, S. Weiss, H. Haemmerle, and E. Zrenner, (1998) "Electrical stimulation of degenerated retina of RCS rats by distally applied spatial voltage patterns," Investigative Ophthalmology & Visual Science, 1998.
(13) Weiss, S., A. Stett, and H. Haemmerle, "Slow potential of the chicken retina evoked by local electrical stimulation with planar microelectrodes," Proc. of the 25th Göttingen Neurobiology Conference, vol. II, 1997.
(14) Stett, A., W. Barth, S. Weiss, E. Zrenner, and H. Haemmerle, "Subretinal stimulation of the chicken retina with spatial voltage patterns," Vision Research, 1998.
(15) Chow, A. and V. Chow, "Subretinal electrical stimulation of rabbit retina," Neuroscience Lett., no. 225, pp. 13–16, 1997.
(16) Majji, A, B., et al., "Long-term histological and electrophysiological results of an inactive epiretinal electrode array implantation in dogs," Investigative Ophthalmology and Vis. Sci., vol. 40, no. 9, pp. 2073–2081, August 1999.

Electrodes
(17) L. S. Robblee and T. L. Rose, "Electrochemical guidelines for selection of protocols and electrode materials for neural stimulation," in *Neural Prost. Fundamental Studies*, W. F. Agnew and D. B. McCreery, Eds. Englewood Cliffs, N.J.: Prentice-Hall, 1990, pp. 26–66.
(18) Bucher, V., M. Graf, M. Stelzle, and W. Nisch, "Electrochemical properties and morphology of poly-crystalline silicon thin film microelectrodes," 4th International Symposium on Electrochemical Impedance Spectroscopy, Aug. 2–9, 1998.
(19) Janitza, T., W. Nisch, and M. Stelzle, "Fast fourier transform impedance spectroscopy for rapid monitoring of cell adhesion and growth on microelectrode arrays," 4th International Symposium on Electrochemical Impedance Spectroscopy, Aug. 2–9, 1998.
(20) Janders, M., U. Egert, M. Stelzle, and W. Nisch, "Novel thin film titanium nitride micro-electrodes with excellent charge transfer capability for cell stimulation and sensing applications. Bridging Disciplines for Biomedicine," Proc. 18th Annual Conference of the IEEE Enigneering in Medicine and Biology Society, 54, 1997.
(21) R. J. Greenberg, T. J. Velte, M. S. Humayun, G. N. Scarlatis, and E. DeJuan Jr., "A computational model of electrical stimulation of the retinal ganglion cell," *IEEE Trans. Biomed. Eng.*, vol. 46, pp. 505–514, May 1999.

Electrode Array
(22) Mohr, A., W. Finger, K. J. Foehr, W. Goepel, H. Haemmerle, and W. Nisch, "Performance of a thin film microelectrode array for monitoring electrogenic cells in vitro," Sensors and Actuators, vol. 34, pp. 265–269, 1996.
(23) Nisch, W., J. Boeck, U. Egert, H. Haemmerle, and A. Mohr, "A thin film microelectrode array for monitoring extracellular neuronal activity in vitro," Biosensors & Bioelectronics, vol. 9, pp. 737–741, 1994.
(24) Haemmerle, H., U. Egert, A. Mohr, an W. Nisch, "Extracellular recording in neuronal networks with substrate integrated microelectrode arrays," Biosensors & Bioelectronic, vol. 9, pp. 691–696, 1994.
(25) Boppart. S A., Wheeler. B C., Wallace C S. "A flexible Perforated Microelectrode Array for Extended Neural Recordings". IEEE Transactions on Biomedical Engineering, 39(1), 1992.

Photodiode Array

(26) G. Peyman, A. Y. Chow, C. Liang, V. Y. Chow, J. I. Perlman, and N. S. Peachey, "Subretinal semiconductor microphotodiode array," Ophthalmic Surg. Lasers, vol. 29, pp. 234–241, 1998.

(27) Troeger, B., E. Guenther, B. Schlosshauer, A. Hoff, and E. Zrenner, "Biocompatibility and long-term stability of components of a multi-photodiode array intended for subretinal implantation," Investigative Ophthalmology & Visual Science, vol. 38, S40, 1997.

(28) Zrenner, E., K. -D. Miliczek, V. P. Gabel, H. G. Graf, E. Guenther, H. Haemmerle, B. Hoefflinger, K. Kohler, W. Nisch, M. Schubert, A. Stett, and S. Weiss, "The Development of subretinal microphotodiodes for replacement of degenerated photoreceptors," Ophthalmic Res., vol. 29, pp. 269–280 1997.

Adjustment of Retinal Implants

(29) Stett, A., S. Weiss, P. Gnauck, M. Stelzle, W. Nisch, H. Haemmerle, and E. Zrenner, "Towards a subretinal implant: investigations of the chip/retina interface," Investigative Ophthalmology & Visual Science (Suppl.), vol 38, p. 41, 1997.

(30) R. Eckmiller, "Learning retina implants with epiretinal contacts," Ophthalmic

(31) Becker, M., R. Eckmiller, and E. Hünermann, "Psychophysical test of a tunable Retina Encoder for Retina Implants," Proc. IJCNN'99, Washington D.C., 1999.

(32) Eckmiller, R., R. Hünermann, and M. Becker, "Exploration of a dialog-based tunable Retina Encoder for Retina Implants," Neurocomputing, vol. 26, pp. 1005–1011, 1999.

(33) Becker, M., M. Braun, and R. Eckmiller, "Retina Implant Adjustment with Reinforcement Learning," Proc. ICASSP8, IEEE Press, vol. II, pp. 1181–1184, 1998.

(34) Hornig, R., and R. Eckmiller, "Towards stimulus optimization for simulated ganglion cell stimulation in retina implants," Investigatory Ophtalmology & Visual Science, vol. 39, no. 4, p. S990, abstr. 4578, Mar. 15, 1998.

(35) Becker, M., M. Braun, and R. Eckmiller, "Retina encoder inversion for retina implant simulation," L. Niklasson, et al (eds), Proc. ICANN98, pp. 791–796, 1998.

(36) Becker, M., and R. Eckmiller, "Spatio-temporal filter adjustment from evaluative feedback for a retina implant," W. Gerstner, et. al. (eds), Artificial Neural Networks—ICANN'97, pp. 1181–1186, 1997.

(37) Hornig, R., and R. Eckmiller, "Simulation of selective ganglion cell stimulation for retina implants," Investigative Ophtalmology & Visual Science, vol. 38, no. 4, p. S41, abstr. 189, Mar. 15, 1997.

(38) Hornig, R., and R. Eckmiller, "Simulation of single cell stimulation for retina implants," Göttingen Neurobiology Conference 1997, vol. II, Georg Thieme Verlag Stuttgart, New York, 1997.

(39) Eckmiller, R., "Concerning the development of retina implants with neural nets," Proc. Int. Conf. Neural Inf. Proc., ICONIP '96, Hong Kong, vol. 1, pp. 21–28, 1996.

(40) Eckmiller, R., "Towards Retina Implants for Improvement of Vision in Humans with Retinitis Pigmentosa—Challenges and first Results," Proc. WCNN '95, Washington, D.C., vol. 1, pp. 228–233, 1995.

(41) Becker, M., "Lernverfahren für die wahrnehmungsbasierte Optimierung sensorischer Neuroimplantste," Universität Bonn, 1999.

Circuits

(42) Liu. W., K. Vichienchom, S. C. DeMarco, C. Hughes, E. McGucken, M. S. Humayun, E. DeJuan, Jr., J. D. Weiland, and R. Greenberg. "A Neuro-stimulus Chip with Telemetry Unit for Retinal Prosthetic Device". IEEE Journal of Solid State Circuits, 35(10):1487–1496, October, 2000.

(43) DeMarco. S C. "The Architecture, Design, and Electromagnetic/Thermal Modeling of a Retinal Prosthesis to Benefit the Visually Impaired'. PhD Thesis, North Carolina State University, EGCR 429/422, 1010 Main Campus Drive, Raleigh, N.C. 27695, December 2002.

(44) Suaning. G J. and Lovell N H. "CMOS neurostimulation ASIC with 100 channels, scalable output, and bidirectional radio-frequency telemetry". IEEE Transactions on Biomedical Engineering, 48(2):248–260, February 2001.

(45) Kim, C. and K. Wise, "A 64-site multishank CMOS low-profile neural stimulating probe," IEEE J. Solid-State Circuits, vol. 31, pp. 1230–1238, September 1996.

(46) Von Arx, J. and K. Najafi, "A wireless single-chip telemetry-powered neural stimulator system," ISSCC Dig. Tech. Papers, 1999.

(47) Liu, W., E. McGuken, K. Vichienchom, M. Clements, E. de Juan, and M. Humayun, "Dual unit visual intraocular prosthesis," Proc. 19$^{th}$ Annu. Int. Conf. IEEE Engineering in Medicine and Biology, pp. 2303–2306, 1997.

(48) Troyk, P. R. and M. A. K. Schwan, "Closed-loop class E transcutaneous power and data link for microimplants," IEEE Trans. Biomed. Eng., vol. 39, pp. 589–599, June 1992.

(49) Tang, Z., B. Smith, J. H. Schild, and P. H. Peckham, "Data transmission from an implantable biotelemeter by load-shift keying using circuit configuration modulator," IEEE Trans. Biomed. Eng., vol. 42, pp. 524–528, May 1995.

(50) K. E. Jones and R. A. Normann, "An advanced demultiplexing system for physiological stimulation," IEEE Trans. Biomed. Eng., vol. 44, pp. 1210–1220, December 1997.

(51) P. E. K. Donaldson, "Experimental visual prosthesis," Proc. IEE., vol. 120, pp. 281–298, 1973.

Circuits (Cohlear Implant)

(52) E. S. Hochmair and I. J. Hochmair Desoyer, "An implanted auditory eight-channel stimulator for the deaf," Med. Biol. Eng. Comput., vol. 19, pp. 141–148, 1981.

(53) P. A. Crosby, P. M. Seligman, and J. F. Patrick et al., "The nucleus multi-channel implantable hearing prosthesis," Acta. Otolaryngol. Suppl. (Stockh), vol. 411, pp. 111–114, 1984.

Coils

(54) Ko, W. H., S. P. Liang, and C. D. F. Fung, "Design of radio-frequency powered coils for implant instruments," Med. Biol. Eng. Comput., vol. 15, pp. 634–640, 1977.

(55) Donaldson, D. de N., and T. A. Perkins, "Analysis of resonant coupled coils in the design of radio frequency transcutaneous links," Med. Biol. Eng. Comput., vol. 21, pp. 612–627, 1983.

(56) Flack, F. C., E. D. James, and D. M. Schlapp, "Mutual inductance of air-cored coils: effect on design of radiofrequency coupled implants," Med. Biol. Eng. Comput., vol. 9, pp. 79–85, 1971.

(57) Zierhofer, C. M. and E. S. Hochmair, "Coil design for improved power transfer efficiency in inductive links," Int. Conf. Engineering in Medicine and Biology, vol. 4, pp. 1538–1539, 1997.

Human Experiments

(58) C. Veraart, J. Delbeke, M. C. Wanet-Defalque, A. Vanlierde, J. D. Legat, and C. Trullemans, "Chronic electrical stimulation of the optic nerve in a retinitis pigmentosa blind volunteer," Invest. Ophthalmol. Vis. Sci., vol. 40, p. S783, 1999.

Other

(59) T. Yagi, N. Ito, M. Watanabe, T. Matsushima, and Y. Uchikawa, "A study on hybrid artificial retina with cultured neural cells and semi-conductor micro-device," in Proc. 1998 IEEE Int. Joint Conf Neural Networks (IJCNN'98), pp. 780–783.

John Wyatt and Joseph Rizzo Publications

(60) Wyatt, J. and J. Rizzo, "Ocular implants for the blind," IEEE Spectrum, pp. 47–53, May 1996.

(61) Rizzo, J. F. and J. Wyatt, "Prospects for a Visual Prosthesis," The Neuroscientist, vol. 3, no. 4, pp. 251–262, 1997.

(62) Grumet, A. E., J. L. Wyatt, Jr., J. F. Rizzo, "Multielectrode stimulation and recording in the isolated retina," Journal of Neuroscience Methods, 101, pp. 31–42, 2000.

(63) Rizzo, J. F., J. Wyatt, J. Loewenstein, S. Kelly and D. Shire, "Perceptual Efficacy of Electrical Stimulation of Human Retina with a Microelectrode Array During Acute Surgical Trials, " submitted to IOVS.

(64) Rizzo, J. F., J. Wyatt, J. Loewenstein, S. Kelly and D. Shire, "Methods for Acute Electrical Stimulation of Retina with Microelectrode Arrays and Measurement of Perceptual Thresholds in Humans," submitted to IOVS.

(65) Ziv, O. R., R. Jensen, J. Wyatt and J. F. Rizzo, "Thresholds for activation of rabbit retina cells with a variable current pulse width," submitted to Visual Neuroscience.

Conference Papers

(66) Loewenstein, J., J. F. Rizzo, J. Wyatt and S. Kelly, "Acute Intraocular Electrical Stimulation of the Human Retina," XIV Int'l. Congress of Eye Research, October, 2000, Santa Fe, N. Mex.

Other Major Publications

(67) Wyatt, J. L., Jr., J. F. Rizzo, A. Grumet, D. Edell, R. J. Jensen, "Development of a Silicon Retinal Implant: Epiretinal Stimulation of Retinal Ganglion Cells in the Rabbit," ARVO Poster Session Abstract, Investigative Ophthalmology and Visual Science, vol. 35, no. 4, 1994, p. 1380.

(68) Narayanan, M. V., J. F. Rizzo, D. Edell, J. L. Wyatt, "Development of a Silicon Retinal Implant: Cortical Evoked Potentials Following Focal Stimulation of the Rabbit Retina with Light and Electricity," ARVO Poster Session Abstract, Investigative Ophthalmology and Visual Science, vol. 35, no. 4, 1994, p. 1380.

(69) Mann, J., D. Edell, J. F. Rizzo, J. Raffel, J. L. Wyatt, "Development of a Silicon Retinal Implant: Microelectronic System for Wireless Transmission of Signal and Power," ARVO Poster Session Abstract, Investigative Ophthalmology and Visual Science, vol. 35, no. 4, 1994, p. 1380.

(70) Miller, S., J. F. Rizzo and J. L. Wyatt, "Development of a Silicon Retinal Implant: Long-Term Biocompatibility of Materials," ARVO Poster Session Abstract, Investigative Ophthalmology and Visual Science, vol. 36, no. 4, 1995, p. 3451.

(71) Rizzo, J. F., S. Miller, J. L. Wyatt and D. Edell, "Development of a Silicon Retinal Implant: Reproducibility of Electrically-Evoked Visual Cortical Responses in Rabbits," ARVO Poster Session Abstract, Investigative Ophthalmology and Visual Science, vol. 36, no. 4, 1995, p. 4264.

(72) Wyatt, J., J. Mann, D. Edell, J. Raffel and J. F. Rizzo, "Development of a Silicon Retinal Implant: Demonstration of Microelectronic System for Optical Transmission of Signal and Power," ARVO Poster Session Abstract, Investigative Ophthalmology and Visual Science, vol. 36, no. 4, 1995, p. 1130.

(73) Rizzo, J. F., S. Miller, T. Denison, T. Herndon and J. L. Wyatt, "Electrically-Evoked Cortical Potentials from Stimulation of Rabbit Retina with a Microfabricated Electrode Array," ARVO Poster Session Abstract, Investigative Ophthalmology and Visual Science, vol. 37, no. 3, March 1995, pp. S707.

(74) Rizzo, J. F. A. Grumet, Edell, D., J. L. Wyatt and R. Jensen, "Single-Unit Recording Following Extracellular Stimulation of Retinal Ganglion Cell Axons in Rabbits," ARVO Poster Session Abstract, Investigative Ophthalmology and Visual Science, vol. 38, no. 4, April 1997, p. s40; also RLE Technical Report 600, July 1996.

(75) Grumet, A. E., J. L. Wyatt, and J. F. Rizzo, "Multi-Electrode Recording and Stimulation of the Salamander Retina In Vitro," The Association for Research in Vision and Ophthalmology Annual Meeting (ARVO), Ft. Lauderdale, Fla., May 1998.

(76) Rizzo, J. F. and J. L. Wyatt, "Retinal Prosthesis," Age-Related Macular Degeneration, J. Berger, S. L. Fine, M. G. Maguire, eds., Mosby Publishers, 1999, pp. 413–432.

(77) Rizzo, J. F., J. Loewenstein and J. Wyatt "Development of an Epiretinal Electronic Visual Prosthesis: The Harvard-Medical Massachusetts Institute of Technology Research Program," Retinal Degenerative Disease and Experimental Theory, pp. 463–47, Kluwer Academic/Plenum Publishers, 1999.

(78) Grumet, A. E., J. F. Rizzo and J. L. Wyatt, "Ten Micron Diameter Electrodes Directly Stimulate Rabbit Retinal Ganglion Cell Axons," The Association for Research in Vision and Ophthalmology Annual Meeting (ARVO), Ft. Lauderdale, Fla., p.734, May 1999.

(79) Socha, M. M., J. D. Moss, M. Shahin, T. Herndon, J. L. Wyatt and J. F. Rizzo, "Mechanical Design and Surgical Implantation of Second Generation Retinal Prosthesis," The Association for Research in Vision and Ophthalmology Annual Meeting (ARVO), Ft. Lauderdale, Fla., p. S735, May 1999.

(80) Moss, J. D., M. M. Socha, J. L. Wyatt and J. F. Rizzo, "Hermetic Encapsulation Testing for a Retinal Prosthesis," The Association for Research in Vision and Ophthalmology Annual Meeting (ARVO), Ft. Lauderdale, Fla., p. S732, May 1999.

(81) Rizzo, J. F., J. Loewenstein, S. Kelly, D. Shire, T. Herndon and J. L. Wyatt, "Electrical Stimulation of Human Retina with a Micro-Fabricated Electrode Array," The Association for Research in Vision and Ophthalmology Annual Meeting (ARVO), Ft. Lauderdale, Fla., p. S783, May 1999.

(82) Grumet, A. E., J. F. Rizzo, J. Wyatt, "In-Vitro Electrical Stimulation of Human Retinal Ganglion Cell Axons," ARVO Poster Session Abstract, Investigative Ophthalmology and Visual Science, vol. 41, no. 4, April–May 2000, p. s10.

(83) Rizzo, J. F., J. Wyatt, J. Loewenstein, S. Kelly, "Acute Intraocular Retinal Stimulation in Normal and Blind Humans," ARVO Lecture Abstract, Investigative Ophthalmology and Visual Science, vol. 41, no. 4, April–May 2000, p. s102.
(84) Shahin, M. E., J. F. Rizzo, J. Wyatt, J. Loewenstein, "Evaluation of External Electrical Stimulation of the Eye as a Screening Test for Acute Intraocular Retinal Stimulation Studies," ARVO Poster Session Abstract, Investigative Ophthalmology and Visual Science, vol. 41, no. 4, April–May 2000, p. s860.
(85) Rizzo, J. F., J. Wyatt, M. Humayun, E. DeJuan, W. Liu, A. Chow, R. Eckmiller, E. Zrenner, T. Yagi, G. Abrams, "Retinal Prosthesis: An Encouraging First Decade with Major Challenges Ahead," Editorial, Ophthalmology, vol. 108, no. 1, January 2001.
(86) Shire, D. B., J. L. Wyatt and J. F. Rizzo, "Progress Toward an Inflatable Neural Prosthesis," ARVO Poster Session Abstract, Investigative Ophthalmology and Visual Science, vol. 42, no. 4, May 2001, p. s812.
(87) Caulfield, R. E., J. L. Wyatt Jr., and J. F. Rizzo, "Calculated Power Limits Affecting Retinal Prosthesis Design," ARVO Poster Session Abstract, Investigative Ophthalmology and Visual Science, vol. 42, no. 4, May 2001, p. s814.
(88) Rizzo, J. F., J. L. Wyatt, J. Loewenstein, S. Kelly and D. Shire, "Accuracy and Reproducibility of Percepts Elicited by Electrical Stimulation of the Retinas of Blind and Normal Subjects," ARVO Lecture Abstract, Investigative Ophthalmology and Visual Science, vol. 42, no. 4, May 2001, p. s942.
(89) Wyatt, J., "Steps toward a microelectronic retinal implant for the blind," $3^{rd}$ World Congress in Neurological Rehabilitation, p. 18, April 2002; also $6^{th}$ International Vitreoretinal Meeting, p. 50, May 2002.
(90) Roach, K., L. Theogarajan and J. Wyatt, "An Electrical Model of Electrode Behavior in Retinal Prostheses," ARVO Lecture Abstract, Investigative Ophthalmology and Visual Science, vol. 43, May 2002.

References on Assembly of Flex Circuits
(91) Schueller, R. D., "Multi Metal Layer Circuit," U.S. Pat. No. 6,507,118
(92) Marcantino, G., "Integrated Circuit Chip Package," U.S. Pat. No. 4,710,798
(93) Gilleo, K., ed., "Handbook of Flexible Circuits," New York: Van Nostrand Reinhold, 1992
(94) Fjelstad, J. "Flexible Circuitry—Technology Background and Important Fundamental Issues," Circuit World, V. 25 No. 2, pp. 6–10, 1999.
(95) Oh, K. W. et al., "A New Flip-Chip Bonding Technique Using Micromachined Conductive Polymer," IEEE Trans. Advanced Packaging, Vol. 22 No. 4 pp. 586–591, 1999
(96) Goodman, C. E. et al., "A Novel Multichip Module Assembly Approach Using Gold Ball Flip Chip Bonding," IEEE Trans. Components, Hybrids, and Manufacturing Technology, Vol. 15, No. 4, pp. 457–464, 1992.

References on Biocompatible Encapsulation Techniques
(97) Jaffe, D., "Encapsulation of Integrated Circuits Containing Beam Leaded Devices With a Silicone RTV Dispersion," IEEE Trans. Parts, Hybrids, and Packaging, Vol. 12, No. 3, pp. 182–187, 1976.
(98) Cech, J. M. et al., "Reliability of Passivated Copper Multichip
(99) Module Structures Embedded in Polyimide," IEEE Trans. Components, Hybrids, and Manufacturing Technology, Vol. 16, No. 7 pp. 752–758, 1993.
(100) Gadre, A. et al., "An Integrated BioMEMS Fabrication Technology," in Proc. 2001 International Semiconductor Device Research Symposium, pp. 186–189.
(101) Kale, V., "A Production Parylene Coating Process for Hybrid Microcircuits," IEEE Trans. Parts, Hybrids, and Packaging, Vol. 13, No. 3, pp. 273–279, 1977.
(102) Fofonoff, T. et al., "Mechanical Assembly of a Microelectrode Array for Use in a Wireless Intracortical Recording Device," in Proc. IEEE-EMB Special Topic Conference on Microtechnology in Medicine and Biology, 2002, pp. 269–272
(103) Walkowiak, B. et al., "Interaction of Body Fluids with Carbon Surfaces," in Proc. 3rd International Conference on Novel Applications of Wide Bandgap Layers, 2001, pp. 75–76
(104) U.S. Pat. No. TBD, Power Efficiency Techniques for Neural Stimulation, Wyatt, Kelly, Rizzo, Submitted Oct. 9, 2002
(105) U.S. Pat. No. 6,368,349, Inflatable neural prosthesis, Wyatt, et al., Issued Apr. 9, 2002
(106) U.S. Pat. No. 6,324,429, Chronically implantable retinal prosthesis, Shire, et al., Issued Nov. 27, 2001
(107) U.S. Pat. No. 6,120,538, Intra-ocular lens system including microelectric components, Rizzo, et al., Issued Sep. 19, 2000
(108) U.S. Pat. No. 5,800,530, Intra-ocular lens system including microelectric components, Rizzo, Issued Sep. 1, 1998
(109) U.S. Pat. No. 5,597,381, Methods for epi-retinal implantation, Rizzo, Jan. 28, 1997
(110) U.S. Pat. No. 5,554,187, Medication dispensing intra-ocular lens system, Rizzo, Issued Sep. 10, 1996
(111) U.S. Pat. No. 5,575,813, Low-pressure neural contact structure, Edell, et al., Issued Nov. 19, 1996
(112) U.S. Pat. No. 5,411,540, Method and apparatus for preferential neuron stimulation, Edell, et al., Issued May 2, 1995
(113) U.S. Pat. No. TBA, Method and apparatus for activating molecules to stimulate neurological tissue, Iezzi, et al., Submitted Apr. 11, 2002
(114) U.S. Pat. No. 5,865,839, Artificial retina, Doorish, Issued Feb. 2, 1999
(115) U.S. Pat. No. 5,836,996, Artificial retina, Doorish, Issued Nov. 17, 1998
(116) U.S. Pat. No. 5,147,284, Device and method for restoration of visual functions, Fedorov, et al., Issued Sep. 15, 1992
(117) U.S. Pat. No. 6,400,989, Adaptive sensory-motor encoder for visual or acoustic prosthesis, Eckmiller, Issued Jun. 4, 2002
(118) U.S. Pat. No. 4,628,933, Method and apparatus for visual prosthesis, Michelson, Issued Dec. 16, 1986
(119) U.S. Pat. No. 6,427,087, Artificial retina device with stimulating and ground return electrodes disposed on opposite sides of the neuroretina and method of attachment, Chow, et al., Issued Jul. 30, 2002
(120) U.S. Pat. No. 6,389,317, Multi-phasic microphotodetector retinal implant with variable voltage and current capability, Chow, et al., Issued May 14, 2002
(121) U.S. Pat. No. 6,230,057, Multi-phasic microphotodiode retinal implant and adaptive imaging retinal stimulation system, Chow, et al., Issued May 8, 2001
(122) U.S. Pat. No. 6,201,234, Optical Operational Amplifier, Chow, et al., Issued Mar. 13, 2001
(123) U.S. Pat. No. 6,075,251, Optical transmitter data compression system, Chow, et al., Issued Jun. 13, 2000

(124) U.S. Pat. No. 6,069,365, Optical processor based imaging system, Chow, et al., Issued May 30, 2000
(125) U.S. Pat. No. 6,020,593, Opsistor transmitter data compression system, Chow, et al., Issued Feb. 1, 2000
(126) U.S. Pat. No. 5,949,064, Opsistor image processor with a reference dector and a reference image, Chow, et al., Issued Sep. 7, 1999
(127) U.S. Pat. No. 5,895,415, Multi-phasic microphotodiode retinal implant and adaptive imaging retinal stimulation system, Chow, et al., Issued Apr. 20, 1999
(128) U.S. Pat. No. 5,837,995, Wavelength-controllable voltage-phase photodiode optoelectronic switch ("opsistor"), Chow, et al., Issued Nov. 17, 1998
(129) U.S. Pat. No. 5,556,423, Independent photoelectric artificial retina device and method of using same, Chow, et al., Issued Sep. 17, 1996
(130) U.S. Pat. No. 5,397,350, Independent photoelectric artificial retina device and method of using same, Chow, et al., Issued Mar. 14, 1995
(131) U.S. Pat. No. 5,024,223, Artificial retina device, Chow, Issued Jun. 18, 1991
(132) U.S. Pat. No. 5,016,633, Artificial retina device, Chow, Issued May 21, 1991
(133) U.S. Pat. No. 5,159,927, Visual prosthesis apparatus and method, Schmid, Issued Nov. 3, 1992
(134) U.S. Pat. No. 4,551,149, Prosthetic vision system, Sciarra, Issued Nov. 5, 1985
(135) U.S. Pat. No. 6,393,327, Microelectronic stimulator array, Scribner, Issued May 21, 2002
(136) U.S. Pat. No. 5,109,844, Retinal Microstimulation, de Juan, et. al., Issued May 5, 1992
(137) U.S. Pat. No. TBA, Device and method for manual retinal vein catheterization, Humayun, et al, Submitted Jan. 3, 2002
(138) U.S. Pat. No. TBA, Package for an implantable medical device, Greenberg, et al., Submitted Mar. 28, 2002
(139) U.S. Pat. No. TBA, Intraocular electrode Greenberg, et al., Submitted Jan. 3, 2002
(140) U.S. Pat. No. 6,165,192, Method and apparatus for intraocular retinal tack inserter, Greenberg, et al., Issued Dec. 26, 2000
(141) U.S. Pat. No. 5,944,747, Method for preferential outer retinal stimulation, Greenberg, et al., Issued Aug. 31, 1999
(142) U.S. Pat. No. 5,935,155, Visual prosthesis and method of using same, Humayun, et al., Issued Aug. 10, 1999
(143) U.S. Pat. No. 5,873,901, Treating retinal damage by implanting thin film optical detectors, Wu, et al., Issued Feb. 23, 1999
(144) U.S. Pat. No. 5,674,263, Optic nerve image output device and method, Yamamoto, Issued Oct. 7, 1997

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A retinal prosthesis, comprising:
an RF coil adapted to be attached to the outside of and moving with an eye to receive power from an external power source;
electronic circuitry adapted to be attached to and moving with the eye and electrically connected to the RF coil;
a light sensitive array electrically connected to the electronic circuitry and adapted to be located within the eye for receiving incident light and for generating an electrical signal in response to the incident light; and
a stimulating array adapted for abutting a retina of the eye and electrically connected to the electronic circuitry to stimulate retinal tissue in response to the electrical signal from the light sensitive array, further comprising wireless control means for specifying, from outside the body of a patient, a transformation in response to the patient's reported perceptions by which electrical signals from the light-sensitive array are transformed into a set of electrical patterns to the stimulating array to influence visual function.

2. The retinal prosthesis of claim 1, wherein said light-sensitive array comprises an array of photo diodes.

3. The retinal prosthesis of claim 1, wherein said stimulating array comprises an electrode array.

4. The retinal prosthesis of claim 1, wherein said power source is a primary RF coil positioned external to a body of a patient and adapted to deliver power to said RF coil adapted to be attached to the eye.

5. The retinal prosthesis of claim 1, wherein all electronics adapted to be positioned within the eye contact the retina within a region defined by a surface area of the retina covered by said stimulating array.

6. The retinal prosthesis of claim 1, wherein the stimulating array, the light-sensitive array, the electronic circuitry, and the RF coil are adapted to be attached to the eye so as to conform with the eye's curvature and movements.

7. The retinal prosthesis of claim 1, wherein said stimulating array and said light-sensitive array form an integral component having interlaced elements.

8. A retinal prosthesis, comprising:
an RF coil adapted to be attached to the outside of and moving with an eye to receive power from an external power source, and wherein the RF coil is adapted to be attached to a temporal side of the eye;
electronic circuitry adapted to be attached to and moving with the eye and electrically connected to the RF coil;
a light sensitive array electrically connected to the electronic circuitry and adapted to be located within the eye for receiving incident light and for generating an electrical signal in response to the incident light;
a stimulating array adapted to be positioned sub-retinally within the eye and electrically connected to the electronic circuitry to stimulate retinal tissue in response to the electrical signal from the light sensitive array; and
wireless control means for specifying, from outside a body of a patient, transformation in response to the patient's recorded perceptions by which electrical signals from the light-sensitive array are transformed into a set of electrical patterns to the stimulating array to influence visual function.

9. A retinal prosthesis, comprising:
an RF coil adapted to be associated with an eye to receive power from an external power source;
electronic circuitry adapted to be attached to and moving with the eye and electrically connected to the RF coil;
a light sensitive array electrically connected to the electronic circuitry and adapted to be located within the eye for receiving incident light and for generating an electrical signal in response to the incident light;
a stimulating array adapted for abutting a retina of the eye and electrically connected to the electronic circuitry to stimulate retinal tissue in response to the electrical signal from the light sensitive array; and wireless control means for specifying, from outside a body of a patient, transformation in response to the patient's perceptions by which electrical signals from the light-sensitive array are transformed into a set of electrical patterns to the stimulating array to influence visual function.

10. A retinal prosthesis comprising:

electronic circuitry adapted to be attached to and moving with an eye;

means for delivering power to the electronic circuitry; and a wide field stimulating array adapted to be positioned sub-retinally within the eye and electrically connected to the electronic circuitry for stimulating retinal tissue, wherein the wide field stimulating array has an area of at least 100 mm$^2$.

11. A retinal prosthesis comprising:

electronic circuitry adapted to be attached to and moving with an eye;

an RF coil adapted to be attached to the outside of and moving with the eye and adapted to receive power from a power source and deliver power to the electronic circuitry;

a stimulating array adapted to be positioned within the eye and electrically connected to the electronic circuitry for stimulating retinal tissue; and a demultiplexor to issue stimulus commands to the stimulating array.

12. The retinal prosthesis of claim 11 wherein the demultiplexor is adapted to be located within the eye.

13. A retinal prosthesis comprising:

electronic circuitry adapted to be attached to and moving with an eye;

means for delivering power to the electronic circuitry;

a stimulating array adapted to be positioned within the eye and electrically connected to the electronic circuitry for stimulating retinal tissue; and reverse telemetry means to monitor neural activity.

14. A retinal prosthesis comprising:

electronic circuitry adapted to be attached to and moving with an eye;

means for delivering power to the electronic circuitry;

a light sensitive array electrically connected to the electronic circuitry for receiving incident light and for generating an electrical signal in response to the incident light;

stimulating array adapted to be positioned within the eye and electrically connected to the electronic circuitry for stimulating retinal tissue;

a transformation algorithm for transforming electrical signals from the light sensitive array into a set of electrical patterns to the stimulating array; and means for altering the transformation algorithm based on inputs from a patient or based on known medical specifications.

15. A retinal prosthesis comprising:

electronic circuitry adapted to be attached to and moving with an eye;

means for delivering power to the electronic circuitry; and a stimulating array adapted to be positioned within the eye and electrically connected to the electronic circuitry for stimulating retinal tissue; wherein size and/or spacing of elements within the stimulating array is selected depending on the retinal tissue to be stimulated.

* * * * *